(12) United States Patent
Mitelberg et al.

(10) Patent No.: US 8,491,472 B2
(45) Date of Patent: Jul. 23, 2013

(54) METHODS AND SYSTEMS FOR SUBMUCOSAL IMPLANTATION OF A DEVICE FOR DIAGNOSIS AND TREATMENT WITH A THERAPEUTIC AGENT

(75) Inventors: Vladimir Mitelberg, Austin, TX (US); Donald K. Jones, Dripping Springs, TX (US); David Y. Yuan, Austin, TX (US); Brett E. Naglreiter, Austin, TX (US); Dennis L. McWilliams, Austin, TX (US); Pankaj J. Pasricha, Houston, TX (US)

(73) Assignees: Apollo Endosurgery, Inc., Austin, TX (US); The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 13/304,055

(22) Filed: Nov. 23, 2011

(65) Prior Publication Data
US 2012/0071812 A1    Mar. 22, 2012

Related U.S. Application Data

(62) Division of application No. 11/776,097, filed on Jul. 11, 2007, now Pat. No. 8,066,689.

(51) Int. Cl.
*A61B 1/32* (2006.01)

(52) U.S. Cl.
USPC .......... 600/207; 604/891.1; 604/57; 600/115; 600/116; 606/191; 606/192

(58) Field of Classification Search
USPC ................ 604/891.1, 890.1, 19, 57, 59, 60, 604/93.01, 96.01, 104, 502, 506, 509; 606/190–192, 198; 623/26.64, 23.65, 23.67; 600/115, 116, 207
See application file for complete search history.

(56) References Cited

U.S. PATENT DOCUMENTS

| | | | |
|---|---|---|---|
| 3,039,468 A | 6/1962 | Price | |
| 3,910,279 A | 10/1975 | Okada et al. | |
| 3,980,861 A | 9/1976 | Fukunaga | |
| 4,222,380 A | 9/1980 | Terayama | |
| 4,271,839 A * | 6/1981 | Fogarty et al. | 606/194 |
| 4,418,692 A | 12/1983 | Guay | |
| 4,445,892 A | 5/1984 | Hussein et al. | |
| 4,630,609 A | 12/1986 | Chin | |
| 4,655,219 A | 4/1987 | Petruzzi | |
| 4,779,611 A | 10/1988 | Grooters et al. | |
| 4,819,633 A | 4/1989 | Bauer et al. | |
| 4,887,598 A | 12/1989 | Berke | |
| 4,907,591 A | 3/1990 | Vasconcellos et al. | |

(Continued)

FOREIGN PATENT DOCUMENTS

| JP | 04-220245 | 8/1992 |
|---|---|---|
| WO | WO02/089655 | 11/2002 |

(Continued)

*Primary Examiner* — Laura A Bouchelle
(74) *Attorney, Agent, or Firm* — Gordon & Jacobson, PC

(57) ABSTRACT

Instruments, systems, implants, and methods are provided for performing submucosal medical procedures in a desired area of the digestive tract using endoscopy. Instruments include a safe access needle injection instrument, a submucosal tunneling instrument, a submucosal dissection instrument, and a mucosal resection device. A submucosal implant device for diagnosing and treating disorders of the body may be implanted. A passive submucosal implant device may take the form of a drug delivery depot in which a therapeutic agent within the depot elutes from the depot according to a predetermined elution profile. An active submucosal implant device may take the form of a drug delivery device that incorporates a self-contained diagnostic system to determine the appropriate delivery time and dosage of a therapeutic agent to be administered.

14 Claims, 37 Drawing Sheets

U.S. PATENT DOCUMENTS

| | | | |
|---|---|---|---|
| 5,009,659 | A | 4/1991 | Hamlin et al. |
| 5,014,708 | A | 5/1991 | Hayashi et al. |
| 5,078,716 | A | 1/1992 | Doll |
| 5,080,660 | A | 1/1992 | Buelna |
| 5,135,484 | A | 8/1992 | Wright |
| 5,150,717 | A | 9/1992 | Rosen et al. |
| 5,158,543 | A | 10/1992 | Lazarus |
| 5,159,925 | A | 11/1992 | Neuwirth et al. |
| 5,195,507 | A | 3/1993 | Bilweis |
| 5,196,024 | A | 3/1993 | Barath |
| 5,226,908 | A | 7/1993 | Yoon |
| 5,290,284 | A | 3/1994 | Adair |
| 5,300,023 | A | 4/1994 | Lowery et al. |
| 5,308,327 | A | 5/1994 | Heaven et al. |
| 5,318,543 | A | 6/1994 | Ross et al. |
| 5,318,564 | A | 6/1994 | Eggers |
| 5,339,799 | A | 8/1994 | Kami et al. |
| 5,370,134 | A | 12/1994 | Chin et al. |
| 5,372,601 | A | 12/1994 | Lary |
| 5,383,889 | A | 1/1995 | Warner et al. |
| 5,395,312 | A | 3/1995 | Desai |
| 5,417,697 | A | 5/1995 | Wilk et al. |
| 5,431,173 | A | 7/1995 | Chin et al. |
| 5,458,583 | A | 10/1995 | McNeely et al. |
| 5,507,744 | A | 4/1996 | Tay et al. |
| 5,507,765 | A | 4/1996 | Mott |
| 5,507,795 | A | 4/1996 | Chiang et al. |
| 5,527,273 | A | 6/1996 | Manna et al. |
| 5,531,699 | A | 7/1996 | Tomba et al. |
| 5,556,405 | A | 9/1996 | Lary |
| 5,570,700 | A | 11/1996 | Vogeler |
| 5,571,130 | A | 11/1996 | Simpson et al. |
| 5,582,609 | A | 12/1996 | Swanson et al. |
| 5,588,951 | A | 12/1996 | Zhu et al. |
| 5,591,183 | A | 1/1997 | Chin |
| 5,599,294 | A | 2/1997 | Edwards et al. |
| 5,599,300 | A | 2/1997 | Weaver et al. |
| 5,628,753 | A | 5/1997 | Cracauer et al. |
| 5,632,746 | A | 5/1997 | Middleman et al. |
| 5,643,305 | A | 7/1997 | Al-Tameem |
| 5,651,788 | A | 7/1997 | Fleischer et al. |
| 5,697,944 | A | 12/1997 | Lary |
| 5,702,438 | A | 12/1997 | Avitall |
| 5,709,224 | A | 1/1998 | Behl et al. |
| 5,713,364 | A | 2/1998 | DeBaryshe et al. |
| 5,718,703 | A | 2/1998 | Chin |
| 5,738,683 | A | 4/1998 | Osypka |
| 5,782,747 | A | 7/1998 | Zimmon |
| 5,782,800 | A | 7/1998 | Yoon |
| 5,800,449 | A | 9/1998 | Wales |
| 5,823,947 | A | 10/1998 | Yoon et al. |
| 5,827,268 | A | 10/1998 | Laufer |
| 5,836,947 | A | 11/1998 | Fleischman et al. |
| 5,868,767 | A | 2/1999 | Farley et al. |
| 5,871,475 | A | 2/1999 | Frassica |
| 5,885,278 | A | 3/1999 | Fleischman |
| 5,887,594 | A | 3/1999 | LoCicero, III |
| 5,891,141 | A | 4/1999 | Rydell |
| 5,913,870 | A | 6/1999 | DeFonzo et al. |
| 5,961,526 | A | 10/1999 | Chu et al. |
| 5,984,939 | A | 11/1999 | Yoon |
| 5,997,536 | A | 12/1999 | Osswald et al. |
| 6,016,452 | A | 1/2000 | Kasevich |
| 6,032,077 | A | 2/2000 | Pomeranz |
| 6,045,570 | A | 4/2000 | Epstein et al. |
| 6,056,763 | A | 5/2000 | Parsons |
| 6,068,603 | A | 5/2000 | Suzuki |
| 6,071,283 | A | 6/2000 | Nardella et al. |
| 6,098,629 | A | 8/2000 | Johnson et al. |
| 6,099,518 | A | 8/2000 | Adams et al. |
| 6,117,101 | A | 9/2000 | Diederich et al. |
| 6,117,148 | A | 9/2000 | Ravo et al. |
| 6,132,428 | A | 10/2000 | VanDusseldorp |
| 6,146,401 | A | 11/2000 | Yoon et al. |
| 6,152,920 | A | 11/2000 | Thompson et al. |
| 6,171,319 | B1 | 1/2001 | Nobles et al. |
| 6,190,382 | B1 | 2/2001 | Ormsby et al. |
| 6,190,384 | B1 | 2/2001 | Ouchi |
| 6,193,129 | B1 | 2/2001 | Bittner et al. |
| 6,258,086 | B1 | 7/2001 | Ashley et al. |
| 6,270,501 | B1 | 8/2001 | Freiberg et al. |
| 6,279,809 | B1 | 8/2001 | Nicolo |
| 6,319,230 | B1 | 11/2001 | Palasis et al. |
| 6,324,418 | B1 | 11/2001 | Crowley et al. |
| 6,346,099 | B1 | 2/2002 | Altman |
| 6,354,297 | B1 | 3/2002 | Eiseman |
| 6,358,262 | B1 | 3/2002 | Chan et al. |
| 6,454,727 | B1 | 9/2002 | Burbank et al. |
| 6,475,226 | B1 | 11/2002 | Belef et al. |
| 6,478,794 | B1 | 11/2002 | Trapp et al. |
| 6,494,881 | B1 | 12/2002 | Bales et al. |
| 6,535,764 | B2 | 3/2003 | Imran et al. |
| 6,572,615 | B2 | 6/2003 | Schulze et al. |
| 6,592,608 | B2 | 7/2003 | Fisher et al. |
| 6,623,494 | B1 | 9/2003 | Blatter |
| 6,626,921 | B2 | 9/2003 | Blatter et al. |
| 6,632,231 | B2 | 10/2003 | Radisch, Jr. |
| 6,645,200 | B1 | 11/2003 | Koblish et al. |
| 6,660,003 | B1 | 12/2003 | DeVore et al. |
| 6,689,130 | B2 | 2/2004 | Arai et al. |
| 6,695,810 | B2 | 2/2004 | Peacock et al. |
| 6,712,775 | B2 | 3/2004 | Burbank et al. |
| 6,736,822 | B2 | 5/2004 | McClellan et al. |
| 6,736,828 | B1 | 5/2004 | Adams et al. |
| 6,743,244 | B2 | 6/2004 | Blatter et al. |
| 6,764,497 | B2 | 7/2004 | Fogarty et al. |
| 6,770,026 | B2 | 8/2004 | Kan et al. |
| 6,796,963 | B2 | 9/2004 | Carpenter et al. |
| 6,852,091 | B2 | 2/2005 | Edwards et al. |
| 6,852,111 | B1 | 2/2005 | Lieber |
| 6,860,892 | B1 | 3/2005 | Tanaka et al. |
| 6,866,676 | B2 | 3/2005 | Kieturakis et al. |
| 6,893,439 | B2 | 5/2005 | Fleischman |
| 6,899,721 | B2 | 5/2005 | Sferco |
| 6,921,361 | B2 | 7/2005 | Suzuki et al. |
| 6,932,833 | B1 | 8/2005 | Sandoval et al. |
| 6,936,014 | B2 | 8/2005 | Vetter et al. |
| 6,936,024 | B1 | 8/2005 | Houser |
| 6,949,099 | B2 | 9/2005 | Shiro et al. |
| 6,951,566 | B2 | 10/2005 | Lary |
| 6,964,660 | B2 | 11/2005 | Maguire et al. |
| 6,971,989 | B2 | 12/2005 | Yossepowitch |
| 6,994,705 | B2 | 2/2006 | Nobis et al. |
| 7,029,471 | B2 | 4/2006 | Thompson et al. |
| 7,063,682 | B1 | 6/2006 | Whayne et al. |
| 7,063,712 | B2 | 6/2006 | Vargas et al. |
| 7,089,045 | B2 | 8/2006 | Fuimaono et al. |
| 7,252,665 | B2 | 8/2007 | Starkebaum et al. |
| 2001/0009985 | A1 | 7/2001 | Durgin et al. |
| 2001/0047177 | A1 | 11/2001 | Kasten |
| 2001/0053909 | A1 | 12/2001 | Nakada et al. |
| 2002/0055757 | A1 | 5/2002 | Torre et al. |
| 2002/0077642 | A1 | 6/2002 | Patel et al. |
| 2002/0139379 | A1 | 10/2002 | Edwards et al. |
| 2002/0165589 | A1 | 11/2002 | Imran et al. |
| 2003/0045811 | A1 | 3/2003 | Hinchliffe et al. |
| 2003/0181901 | A1 | 9/2003 | Maguire et al. |
| 2004/0148034 | A1 | 7/2004 | Kagan et al. |
| 2005/0038462 | A1 | 2/2005 | Lubock et al. |
| 2005/0149099 | A1 | 7/2005 | Yamano et al. |
| 2005/0209653 | A1 | 9/2005 | Herbert et al. |
| 2005/0222567 | A1 | 10/2005 | Ouchi |
| 2005/0234294 | A1 | 10/2005 | Saadat et al. |
| 2005/0247320 | A1 | 11/2005 | Stack et al. |
| 2006/0095079 | A1* | 5/2006 | Gerber ............ 607/2 |
| 2006/0100614 | A1 | 5/2006 | Long |
| 2006/0189889 | A1 | 8/2006 | Gertner |

FOREIGN PATENT DOCUMENTS

| | | |
|---|---|---|
| WO | WO02/089655 A2 | 11/2002 |
| WO | WO 02089655 A2 * | 11/2002 |
| WO | WO03/013625 A2 | 2/2003 |
| WO | WO2006/074060 | 7/2006 |
| WO | WO2007067919 A2 | 6/2007 |
| WO | WO2007067919 A3 | 6/2007 |

* cited by examiner

METHODS AND SYSTEMS FOR SUBMUCOSAL IMPLANTATION OF A DEVICE FOR DIAGNOSIS AND TREATMENT WITH A THERAPEUTIC AGENT

CROSS-REFERENCE TO RELATED APPLICATION

This application is a divisional of U.S. Ser. No. 11/776,097, filed Jul. 11, 2007, now issued as U.S. Pat. No. 8,066,689, which is hereby incorporated by reference herein in its entirety.

FIELD OF THE INVENTION

The present invention relates to a safe access needle injection instrument, a submucosal tunneling instrument, a submucosal dissection instrument, a submucosal implant device a system and a method for performing submucosal medical procedures in a desired area of the digestive tract using an endoscope. One aspect in particular relates to the implantation of a device in the submucosal layer of the digestive tract for diagnosing or treating disorders of the body.

BACKGROUND OF THE INVENTION

The field of gastrointestinal endoscopy has for many years focused on diagnostic and therapeutic techniques to observe, modify and remove tissues located in the digestive tract. General endoscopic procedural techniques such as visualizing, dilating, cutting and manipulating tissue have been accomplished using flexible devices such as endoscopes, balloons, snares and electrosurgical tools well known in the art.

While many of these devices and techniques have been useful in identifying and removing some neoplastic lesions of the mucosal layer as well as providing access to general locations within the digestive tract for the placement of submucosal implants, there are some lesions and areas of the digestive tract which are extremely difficult to resect or access. For example, the en bloc removal of large flat mucosal lesions presents numerous problems for current endoscopic tools and techniques. In addition, to effectively diagnosis some disorders (gastric motility, irritable bowel syndrome, chronic intestinal pseudo-obstruction, etc.) a biopsy of the muscular wall or the myenteric plexus may be necessary. Currently, access to these types of specimens requires full thickness biopsies which can be particularly difficult from an endoscopic approach requiring extremely skilled closure techniques.

There have been some advances in endoscopic techniques to resect flat lesions of the mucosal layer generally termed, Endoscopic Mucosal Resection (EMR). One of these EMR techniques, "lift and cut", involves the injection of saline or other biocompatible solution beneath the lesion in an attempt to raise the lesion thereby changing the geometry to make it suitable for resection using conventional snare devices.

Modifications to this technique are disclosed in U.S. Pat. No. 5,651,788 in which a lesion is identified and an injection catheter is used to inject saline to elevate the lesion. A ligator is attached to the distal end of the endoscope and suction is applied to the lesion to bring the tissue into the ligator. A ligator band is then applied to the tissue to form a banded mushroom-like polyp which is suitable for removal with an electrosurgical snare.

Alternatively U.S. Pat. No. 5,961,526 discloses a coaxial needle and severing snare assembly in which a needle is used to pierce tissue adjacent a target lesion to elevate the lesion with saline. Once the lesion is elevated, the needle is retracted from the tissue and the snare is extended from the needle lumen to surround the lesion. The lesion is then aspirated into an aspiration cylinder adjacent the distal end of the endoscope and the snare is cinched to sever the tissue surrounding the lesion.

While EMR techniques have been shown to be effective in treating some flat neoplastic lesions there are limitations and complications associated with these techniques. A major limitation associated with this technique is the size of the lesion that can be resected. Generally, these EMR techniques are suitable only for resecting mucosal lesions which are less than 2 cm in diameter. While larger or irregular shaped lesions may be resected in a piecemeal fashion, this is undesirable since small portions of the lesion may remain. Another limitation of these techniques includes uncertainty of the area being resected. Once tissue has been suctioned into a cap ligator or aspiration cylinder, the tissue is directly adjacent the visualization means of the endoscope obscuring the field of view. One complication associated with these EMR techniques is in relation to the use of the needle injection system. Manipulating the injection catheter to position the needle through the mucosal layer into the submucosal layer can ultimately result in puncturing the muscular wall of the digestive tract which may lead to infection or peritonitis. Another complication associated with EMR techniques is damage to the underlying muscular layer. Saline and other non-viscous fluids used to elevate the lesion dissipate relatively quickly after injection into the submucosal layer, such that portions of the underlying muscular layer may be included in the suctioned tissue and inadvertently damaged when using the electrosurgical tool for resection.

In order to overcome some of the size, irregular shapes and visualization limitations associated with EMR techniques, a new procedure called Endoscopic Submucosal Dissection (ESD) has been developed. With this procedure the periphery of the target resection area, which includes the lesion, is marked. An injection catheter is used to deliver a viscous fluid within the submucosal layer, which does not readily dissipate, throughout the target resection area. Once the target resection area has been elevated, an incision is made through the mucosal layer at the edge of the resection area using an electrosurgical needle knife. The physician uses the needle knife to cut the mucosal layer along the periphery of the target resection area. Once the boundary of the resection area has been cut, the physician then uses the needle knife to manually cut the submucosal connective tissue binding the mucosal layer to the muscular wall. Once the physician has completed the submucosal dissection, the mucosal layer is free to be removed in one piece. While this procedure allows the physician to resect large, irregular shaped lesions en bloc, it requires a high degree of skill on the part of the physician and is still subject to the complications associated with needle perforations and muscular layer injury.

In performing the ESD method of resecting a neoplastic lesion, as well as, performing a submucosal medical procedure it is apparent that dissecting the connective tissue of the submucosal space is an important step in having a successful outcome. Numerous investigators have attempted to provide ways of dissecting the submucosal connective tissue.

In U.S. Pat. No. 6,098,629 a method of implanting a submucosal esophageal bulking device is disclosed. The patent further discloses the use of a blunt dissecting member to create a submucosal pocket. In addition, the patent discloses the use of a balloon inserted into the submucosal layer to dissect the submucosal tissue when dilated to form a submucosal pocket.

In PCT Patent Application No. WO 02/089655, methods of implanting submucosal gastric implants are disclosed. The application further discloses various configurations of mechanical and electrosurgical dissection instruments for dissecting the connective tissue of the submucosal layer to form a submucosal pocket in which to place a gastric implant. Included in the description of mechanical dissection instruments are various configurations of balloon dissection instruments.

In U.S. Patent Application No. US2005/0149099, a submucosal dissection instrument, system and method are disclosed. The application further discloses an electrosurgical high frequency knife in combination with a submucosal dissection balloon. Included in the method are the steps of sequentially activating the high frequency knife to create a hole and advancing the balloon assembly into the hole with expansion of the balloon dissecting the connective tissue of the submucosal layer. These steps of the method are repeated until all of the connective tissue beneath the lesion is completely dissected.

With most of the aforementioned disclosed submucosal dissection techniques the physician is required to initially advance a significant portion of a dissection instrument into the submucosal layer while the connective tissue is generally intact. These techniques require that a pushing force be transmitted to the tip of the instrument to dissect the submucosal connective tissue. During application of this pushing force there is a risk that the tip of the instrument may injure or perforate the muscular wall or the mucosal layer.

In performing the disclosed method using the electrosurgical high frequency knife the initial hole through the mucosal layer may be visualized endoscopically. Once the balloon assembly is advanced into the submucosal incision hole and expanded to create a cavity, further advancement of the high frequency knife to form a second hole must be conducted without visualization. During the second hole formation and subsequent holes, without visual confirmation of the orientation of the high frequency knife there is a risk of perforating the muscular wall or mucosal layer.

SUMMARY OF THE INVENTION

In accordance with one aspect of the present invention there is provided a safe access needle injection instrument for use in a mammal. The safe access needle injection instrument includes an elongated flexible tubular member with proximal and distal ends and a lumen extending therethrough. A tissue holding member is positioned adjacent the distal end of the tubular member. A needle member having proximal and distal ends with a lumen extending therethrough is slidably positioned within the lumen of the tubular member.

The tissue holding member is integrally formed with the tubular member and is in the form of a window member adapted to engage the mucosal tissue within the digestive tract. A seal plug is included within the lumen of the tubular member distal to the window member. When a vacuum source connected to the proximal end of the tubular member is activated the vacuum causes the mucosal tissue to be suctioned within the window member of the tissue holding member.

The needle member is coaxially disposed within the lumen of the tubular member. The distal end of the needle member is operable from a first position proximal to the window member to a second position within the window member by axially advancing the needle member relative to the tubular member. Similarly, the distal end of the needle is operable from a second position within the window member to a first position proximal to the window member by axially retracting the needle member relative to the tubular member. When a vacuum is applied to the tubular member, the mucosal tissue is suctioned within the window member of the tissue holding member. The distal end of the needle member operated from its first position to the second position to thereby pierce the mucosal layer of the tissue and enter the submucosal layer.

In accordance with another aspect of the present invention there is provided a safe access needle injection instrument for use in a mammal. The safe access needle injection instrument includes an elongated flexible tubular sheath member with proximal and distal ends and a lumen extending therethrough. A tissue holding member is positioned adjacent the distal end of the tubular sheath member. A needle member having proximal and distal ends with a lumen extending therethrough is slidably positioned within the lumen of the tubular sheath member.

The tissue holding member takes the form of a pair of operable jaws connected to the distal end of an elongate shaft member. The jaws are adapted to engage the mucosal tissue within the digestive tract. The elongate shaft member is slidably disposed within the lumen of the tubular sheath member. The jaws are operable from an open configuration in which the jaws are biased outwardly when unconstrained, to a closed configuration in which the jaws approach each other when partially or fully constrained. When the tissue holding member is positioned adjacent the distal end of the tubular sheath member and the jaws are unconstrained, proximal movement of the elongate shaft member relative to the distal end of the tubular sheath, causes the jaws to be partially constrained and move from the open configuration to the closed configuration.

The needle member is coaxially disposed within the lumen of the tubular member. The distal end of the needle member is operable from a first position proximal to the tissue holding member jaws to a second position between the tissue holding member jaws, by axially advancing the needle member relative to the elongate shaft member. Similarly, the distal end of the needle is operable from a second position between the tissue holding member jaws to a first position proximal to the tissue holding jaws by axially retracting the needle member relative to the elongate shaft member. When the jaws of the tissue holding member are positioned adjacent the mucosal tissue and are operated from an open to closed configuration, mucosal tissue is grasped and held between the jaws. The distal end of the needle member is then operated from the first position to the second position to thereby pierced the mucosal layer of the tissue and enter the submucosal layer.

In accordance with another aspect of the present invention, the needle member further includes a stop member positioned adjacent the distal end of the needle member. When the distal end of the needle member pierces the mucosal layer, the stop member engages the mucosal tissue to thereby limit the depth to which the needle penetrates through the mucosal layer. Once the stop member engages the mucosal tissue it may also seal around the needle such that fluid injected through the lumen of the needle into the submucosal layer does not exit the puncture site of the needle.

In accordance with a further aspect of the present invention, a method is provided for operating a safe access needle instrument to create a safety bleb beneath the mucosal layer in the digestive tract of a mammal. The method includes the step of providing a safe access needle injection instrument. The safe access needle injection instrument having a tubular member, tissue holding member and a needle member slidably disposed within the lumen of the tubular member. The method also includes the step of inserting the safe access needle injection instrument through a natural orifice into the digestive tract of a mammal. The method additionally includes the step operating the safe access needle injection instrument to engage mucosal tissue with the tissue holding member. The method also includes the step of piercing the mucosal layer with the needle member. The method further includes the step of injecting fluid through the needle member into the submucosal layer.

In accordance with another aspect of the present invention there is provided a safe access dissection system for use in a mammal. The safe access dissection system includes safe access needle injection instrument and an injectable dissection material. The injectable dissection material may take the form of a solution capable of dissolving the submucosal connective tissue. An example of this type of dissolving solution is sodium 2-mercaptoethanesulfanate (MESNA). Additional substances which may dissolve the submucosal connective tissue include acids and enzymes such as a peptase enzyme solution, protease/collagenase, papain, chymotrypsin and acetylcycteine. The injectable dissection material may take the form of a non-pharmacological agent and provide a pure mechanical dissection of the submucosal tissue. The mechanical injectable dissection material includes injectable solutions which solidify upon entering the submucosal space, injectable semisolid gelatins, and injectable gelled microspheres. Solutions which solidify after injection into the submucosal space may be thermosensitive polymer solutions such as Pluronic 127. Additional injectable solidifying solutions include monomer and polymer solutions like hydrogels and cyanoacrylates which polymerize or crosslink upon contact with tissue or added chemical agents. The semisolid gelatins and gelled microspheres may be formed of natural materials such as collagen and alginates or synthetic materials like polyvinylalcohol (PVA), polyvinylpyrolidone (PVP) and acrylate polymers.

In accordance with a further aspect of the present invention, a method is provided for operating a safe access dissection system to create a dissected safety bleb beneath the mucosal layer in the digestive tract of a mammal. The method includes the step of providing a safe access needle injection instrument and a dissecting material. The safe access needle injection instrument having a tubular member, tissue holding member and a needle member slidably disposed within the lumen of the tubular member. The method also includes the step of inserting the safe access needle injection instrument through a natural orifice into the digestive tract of a mammal. The method additionally includes the step operating the safe access needle injection instrument to engage mucosal tissue with the tissue holding member. The method also includes the step of piercing the mucosal layer with the needle member. The method further includes the step of injecting a dissecting material through the needle member into the submucosal layer where the submucosal connective tissue is dissected, separating the mucosal layer from the muscular layer. The method may additionally include the step of removing the dissecting material from the mammal.

In accordance with an aspect of the present invention, there is provided a submucosal tunneling instrument. The submucosal tunneling instrument includes an elongate tubular member having proximal and distal ends and a lumen extending therethrough and an elongate expandable member located at the distal end of the tubular member. The expandable member has proximal and distal ends wherein the proximal end of the expandable member is connected to the distal end of the tubular member. The expandable member is everted, such that the distal end of the expandable member is positioned within the lumen of the tubular member.

In accordance with an aspect of the present invention, there is provided a submucosal tunneling instrument. The submucosal tunneling instrument includes an elongate tubular member having proximal and distal ends and a lumen extending therethrough and an elongate expandable member located at the distal end of the tubular member. The expandable member has proximal and distal ends wherein the proximal end of the expandable member is connected to the distal end of the tubular member. The expandable member has a first spiral configuration, in which the distal end of the expandable member is positioned within center of the rolled spiral shape, and a second extended configuration in which the proximal and distal ends of the expandable member generally take the form of a straight line shape. The expandable member is operable from a first spiral configuration to a second extended configuration. The expandable member may also include a retaining member which maintains the shape of the expandable member in its first spiral configuration during delivery and positioning of the submucosal tunneling instrument. The retaining member may take the form of a spiral shaped coil member affixed to the balloon. The spiral shaped coil member may be formed from metals or polymers which may be resilient or non-resilient.

In accordance with yet another aspect of the present invention, the submucosal tunneling instrument expandable member takes the form of a balloon. The balloon may be of the compliant or non-compliant type generally known in the art. The balloon may be formed from biocompatible polymer types such as olefins, elastomers, thermoplastic elastomers, vinyls, polyamides, polyimides, polyesters, fluropolymers, copolymers and blends of any of the aforementioned.

In accordance with still another aspect of the present invention, the expandable member takes the form of a tubular framework. The tubular framework may be constructed in different fashions such as a laser cut tube, braided and non braided mesh tubes. The tubular framework may be formed from polymers such as olefins, thermoplastic elastomers, vinyls, polyamides, polyimides, polyesters, fluropolymers, copolymers and blends of any of the aforementioned or metals such as stainless steel, nitinol and other biocompatible metallic alloys.

In accordance with another aspect of the present invention the distal end of the expandable member is connected to the distal end of a tether member. The tether member is slidably disposed with the lumen of the tubular member and has a proximal end which is connected to a handle member. The tether member takes the form of a flexible filament which may include a through lumen. The handle member may be used to adjust the length of the tether member to thereby control the length of the expandable member that is allowed to exit the lumen of the tubular member.

In accordance with a further aspect of the present invention, a method is provided for operating a submucosal tunneling instrument to create a submucosal tunnel beneath the mucosal layer in the digestive tract of a mammal. The method includes the step of creating a safety bleb beneath the mucosal layer. The method also includes the step of providing a submucosal tunneling instrument. The submucosal tunneling instrument has an elongate tubular member, and an everted expandable member located within the distal lumen of the tubular member. The method also includes the step of inserting the submucosal tunneling instrument through a natural orifice into the digestive tract of a mammal. The method additionally includes the step of forming an opening in the mucosal layer of the safety bleb. The method also includes the step of positioning the distal end of the submucosal tunneling instrument through the formed opening in the mucosal layer.

The method further includes the step of operating the submucosal tunneling instrument to thereby extend and expand the expandable member from the tubular member, thereby forming a submucosal tunnel. The method then includes the step of removing the submucosal tunneling instrument from the mammal.

In accordance with another aspect of the present invention there is provided a submucosal tunneling system that includes a safe access needle injection instrument, a submucosal tunneling instrument. The submucosal tunneling system may be provided in the form of a kit.

In accordance with still another aspect of the present invention there is provided a submucosal dissecting instrument. The submucosal dissecting instrument includes an elongate tubular shaft member having proximal and distal ends and a lumen extending therethrough and an expandable member located at the distal end of the tubular shaft member. The submucosal dissecting instrument may further include a marker or markers spaced apart known distances on the shaft of the tubular member to visually determine the length to which the distal end of the tubular member has been inserted into a submucosal tunnel. The markers may additionally be made of radio-opaque material to thereby be visible under fluoroscopy.

In accordance with still yet another aspect of the present invention, the expandable member of the submucosal dissecting instrument takes the form of a balloon. The balloon may be of the compliant or non-compliant type generally known in the art. The balloon may be formed from biocompatible polymer types such as olefins, elastomers, thermoplastic elastomers, vinyls, polyamides, polyimides, polyesters, fluoropolymers, copolymers and blends of any of the aforementioned.

In accordance with a further aspect of the present invention, a method is provided for operating a submucosal dissecting instrument to create a large mucosal layer dissected area in the digestive tract of a mammal. The method includes the step of forming an elongate submucosal tunnel beneath the mucosal layer. The method also includes the step of providing a submucosal dissecting instrument. The submucosal dissecting instrument has an elongate tubular member, and an expandable member located at the distal end of the tubular member. The method also includes the step of inserting the submucosal dissecting instrument through a natural orifice into the digestive tract of a mammal. The method additionally includes the step of positioning the distal end of the submucosal dissecting instrument through an opening formed in the mucosal layer into an elongate submucosal tunnel. The method further includes the step of operating the submucosal dissecting instrument to thereby dilate the expandable member at the distal end of the tubular member, thereby forming a large mucosal layer dissected area. The method then includes the step of removing the submucosal dissecting instrument from the mammal.

In accordance with a further aspect of the present invention there is provided a submucosal tunneling and dissecting instrument. The submucosal tunneling and dissecting instrument includes an elongate first tubular member having proximal and distal ends and a lumen extending therethrough and an elongate first expandable member located at the distal end of the first tubular member. The first expandable member has proximal and distal ends wherein the proximal end of the first expandable member is connected to the distal end of the first tubular member. The first expandable member is everted, such that the distal end of the first expandable member is positioned within the lumen of the first tubular member. The submucosal tunneling and dissecting instrument also includes a second elongate tubular member having proximal and distal ends and a lumen extending therethrough and a second expandable member located at the distal end of the second tubular member. The elongate first tubular member is slidably disposed within the lumen of the elongate second tubular member, such that the distal end of the first tubular member may extend from the distal lumen of the second tubular member.

In accordance with another aspect of the present invention there is provided a submucosal dissection system that includes a safe access needle injection instrument, a submucosal tunneling instrument and a submucosal dissecting instrument. The submucosal dissection system may be provided in the form of a kit. The submucosal dissection system may include a submucosal tunneling instrument and a submucosal dissecting instrument which are integrally formed.

In accordance with another aspect of the present invention there is provided a submucosal implant device for diagnosing and treating disorders of the body. The submucosal implant device may be a passive or active device. A passive submucosal implant device may take the form of a drug delivery depot in which a therapeutic agent within the depot elutes from the depot according to a predetermined elution profile. An active submucosal implant device may take the form of a drug delivery device that incorporates a self contained diagnostic system to determine the appropriate delivery time and dosage of a therapeutic agent to be administered. The passive or active submucosal implant that takes the form of a drug delivery device may include a port positioned through the mucosal layer to allow endoscopic refilling of the drug delivery device with therapeutic agents. The submucosal implant may include an anchor member in which to secure the implant to the muscular wall beneath the mucosal layer.

In accordance with yet another aspect of the present invention there is provided a method for performing a submucosal medical procedure to deploy a submucosal implant device in the digestive tract of a mammal. The method includes the step of forming a submucosal tunnel beneath the mucosal layer in the digestive tract. The method also includes the step of providing a submucosal implant device. The method includes the step of inserting an endoscope through a mucosal opening into the area beneath the mucosal layer. The method also includes the step of positioning a submucosal implant device in the area beneath the mucosal layer. The method additionally includes the step of releasing the submucosal implant device beneath the mucosal layer. The method also additionally includes the step of closing the mucosal opening. The method then includes the step of removing the endoscope from the mammal.

DETAILED DESCRIPTION OF THE INVENTION

Methods and devices for performing submucosal medical procedures in a desired area of the digestive tract using an endoscope are described.

Figure 1:
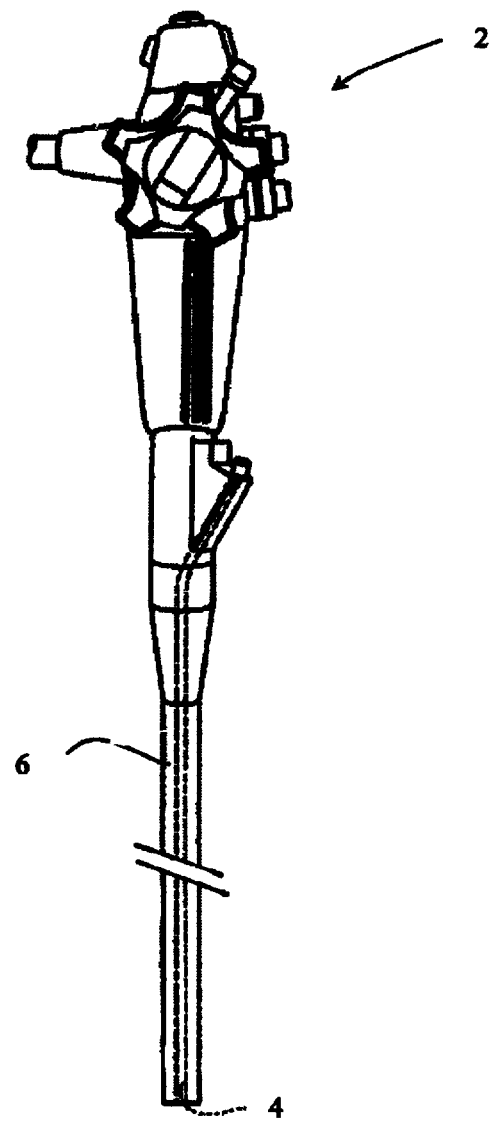
FIG. 1 is a side view of an endoscope of a submucosal medical procedure system according to an embodiment of the present invention.

FIG. 1 illustrates an endoscope 2 of the type used in endoscopic procedures and suitable for use with embodiments of the present invention. The endoscope 2 has a working channel 4 extending from a proximal portion of the endoscope to the distal end of the endoscope. The endoscope 2 also has an insertion section 6 which enters the body of a patient passing through a natural orifice such as the mouth or rectum. The insertion section 6 is generally navigated to a position with the digestive tract when performing a submucosal medical procedure. Devices for use in performing submucosal medical procedures are preferably delivered through working channel 4 of the endoscope 2; however devices may be delivered along side the insertion section 6 of the endoscope.

Figure 2:
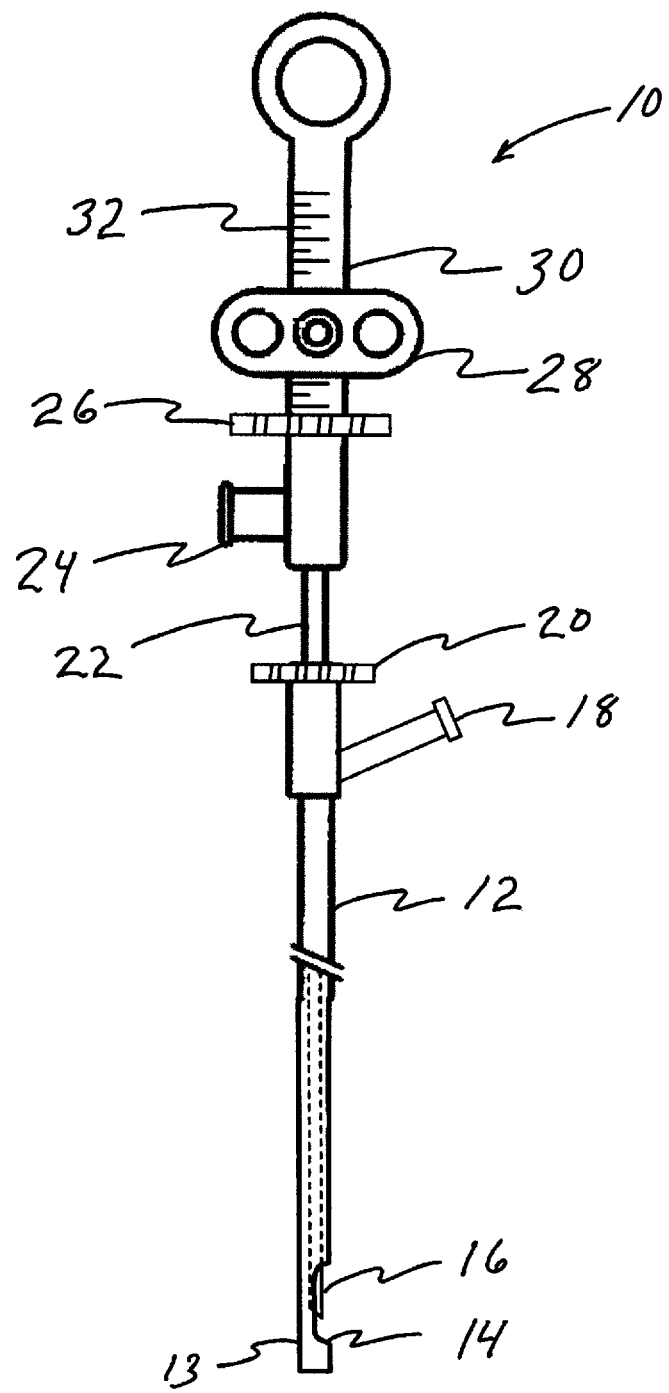
FIG. 2 is a side view of a safe access needle injection instrument according to an embodiment of a submucosal medical procedure system of the present invention.

FIG. 2 illustrates a safe access needle injection instrument 10 which is used to aid the physician in obtaining access to the submucosal layer to perform a submucosal medical procedure. The safe access needle injection instrument 10 includes a tubular shaft 12 having a distal end 13. The diameter of tubular shaft 12 is generally in the range 1 mm to 10 mm with a preferred range of 2.0 to 6.0 mm. Adjacent distal end 13, a portion of the wall of tubular shaft 12 is removed to form window member 14. Alternatively, window member 14 can be formed with a cap element coupled to the distal end of the tubular shaft 12. Slidably disposed within the lumen of tubular shaft 12 is needle member 16. The proximal portion of tubular shaft includes vacuum port 18 which is capable of being coupled to a vacuum source such as a syringe or vacuum pump (not shown). Valve assembly 20 provides a releasable seal to tubular shaft 12. A handle assembly 21 is connected to tubular shaft 12 through connector tubing 22. The handle assembly 21 includes needle fluid port 24 and valve assembly 26 for injecting fluid through and sealing around the proximal portion of needle member 16. The proximal portion of needle member 16 is also connected to a needle slide member 28 positioned on handle body 30. The proximal movement of needle slide member 28 on handle body 30 causes needle member 16 to move proximally within tubular shaft 12. Distance markers 32 are located on handle body 30 to gauge the movement of needle member 16 within tubular shaft 12.

Figure 3:
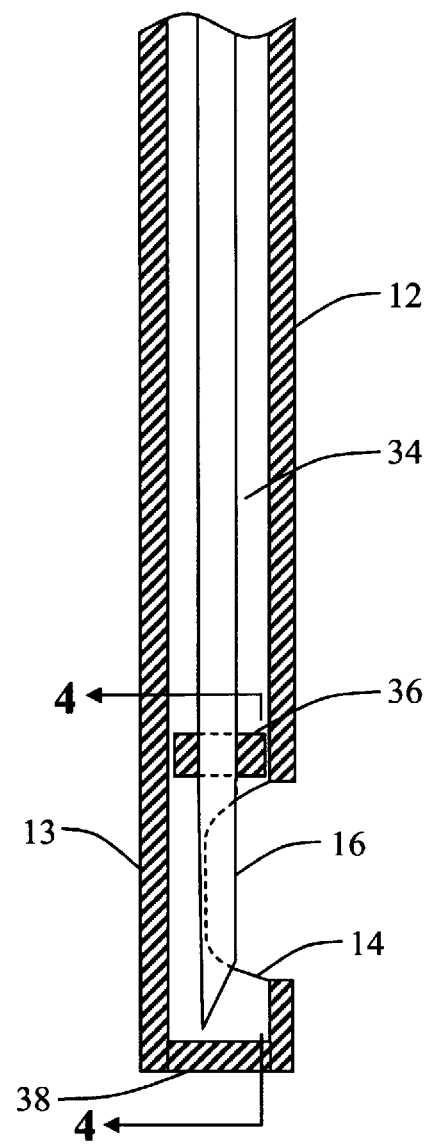
FIG. 3 is a partial cross-sectional view of a safe access needle injection instrument according to an embodiment of a submucosal medical procedure system of the present invention.
Figure 4:
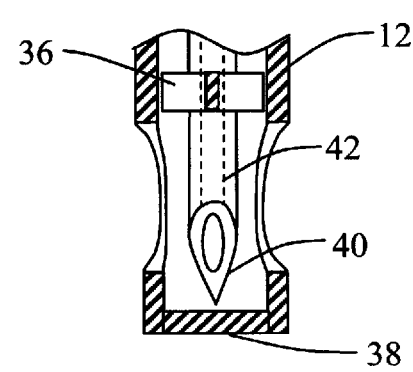
FIG. 4 is a cross-sectional view taken along 4-4 of FIG. 3.

As shown in FIGS. 3 and 4, needle member 16 is positioned within lumen 34 of tubular shaft 12. Located on the exterior of needle member 16 is stop member 36. The distal end 13 of tubular shaft 12 is closed with seal plug 38. Also shown is needle member tip 40 and needle lumen 42. Needle lumen 42 communicates needle tip 40 with needle fluid port 24 so that fluid injected through needle port 24 exits the lumen at needle tip 40.

Figure 5A:
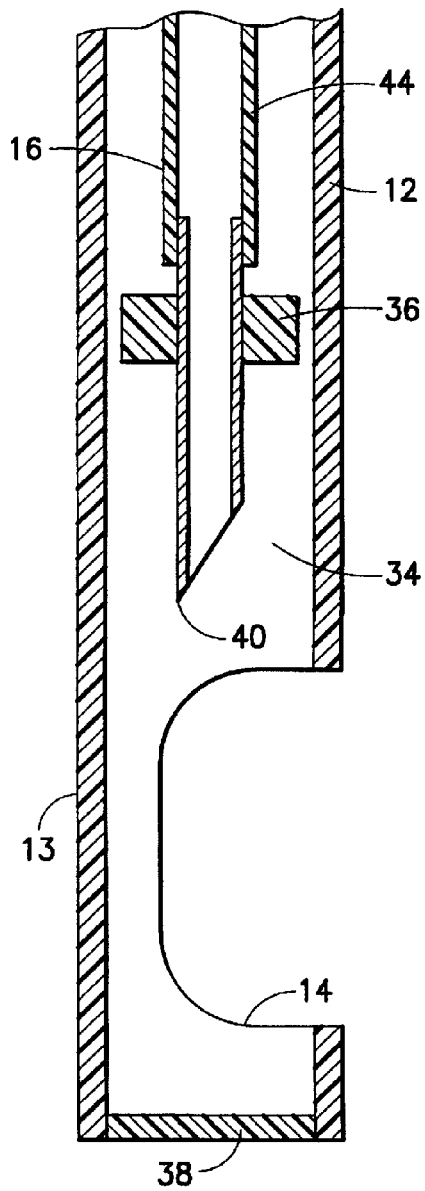
FIG. 5A is a partial cross-sectional view showing a first position of the needle of a safe access needle injection instrument according to an embodiment of a submucosal medical procedure system of the present invention.
Figure 5B:
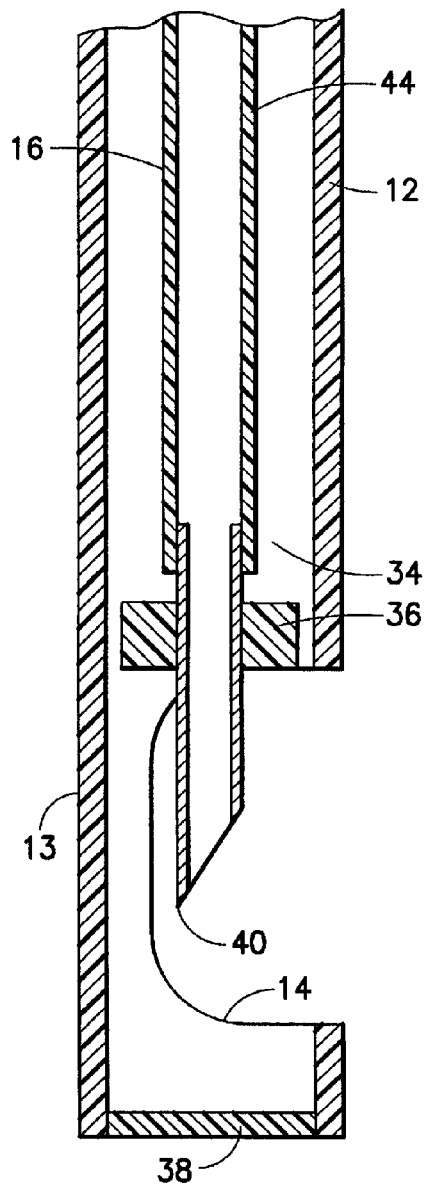
FIG. 5B is a partial cross-sectional view showing a second position of the needle of a safe access needle injection instrument according to an embodiment of a submucosal medical procedure system of the present invention.

FIGS. 5A and 5B, illustrate the actuation of needle member 16. Needle member 16 is shown in detail with needle body 44 connected to needle tip 40. Needle body 44 may be constructed of a separate material as shown or integrally formed with needle tip 40. Needle body 44 may be constructed from flexible tubing having good axial pushability. As shown in FIG. 5A, needle member 16 is in a first position in which needle tip 40 is located within lumen 34 proximal to window member 14. This is the preferred position for needle member 16 when tubular shaft 12 is deployed within the body. Upon actuation, needle member 16 is moved to a second position in which needle tip 40 is positioned within window member 14.

Figure 6A:
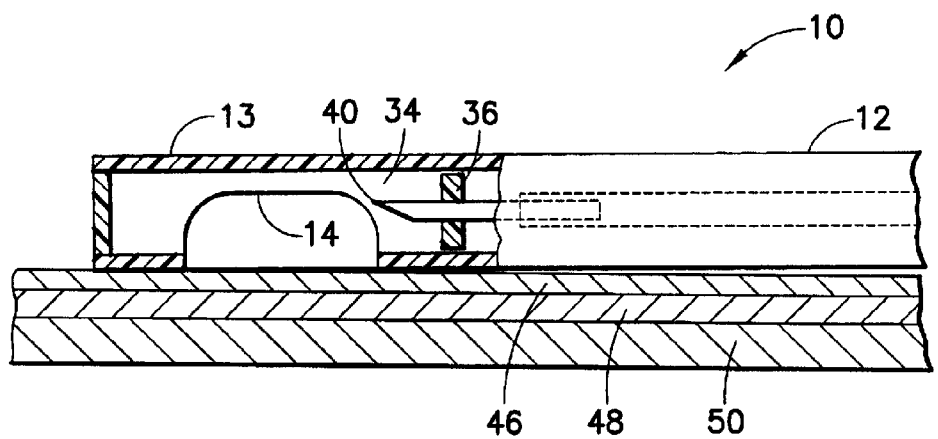
FIG. 6A through 6E are cross-sectional views showing a method creating a submucosal bleb using the safe access needle injection instrument in accordance with an embodiment of the present invention.
Figure 6B:
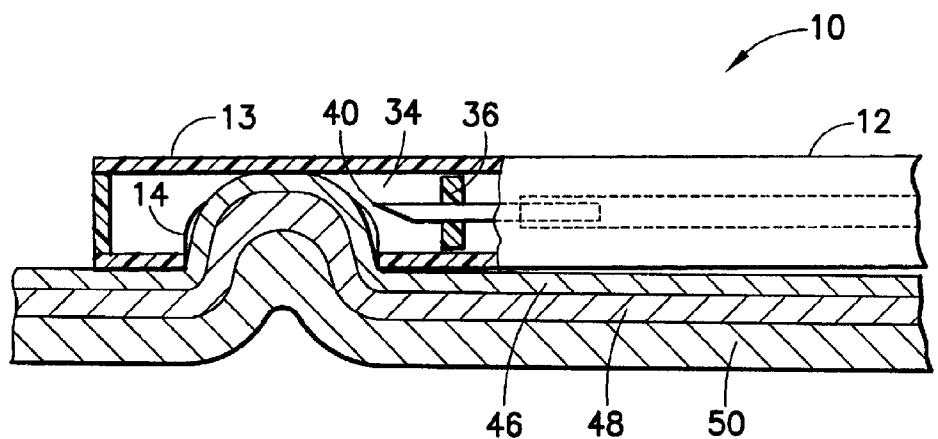
Figure 6C:
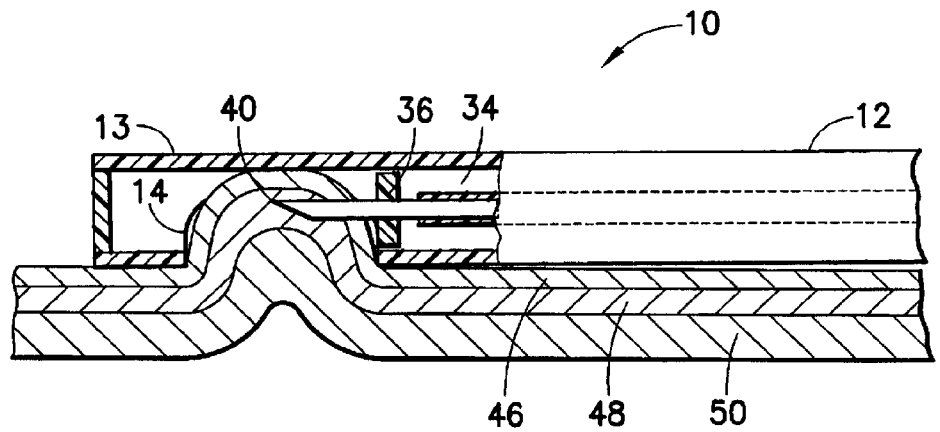
Figure 6D:
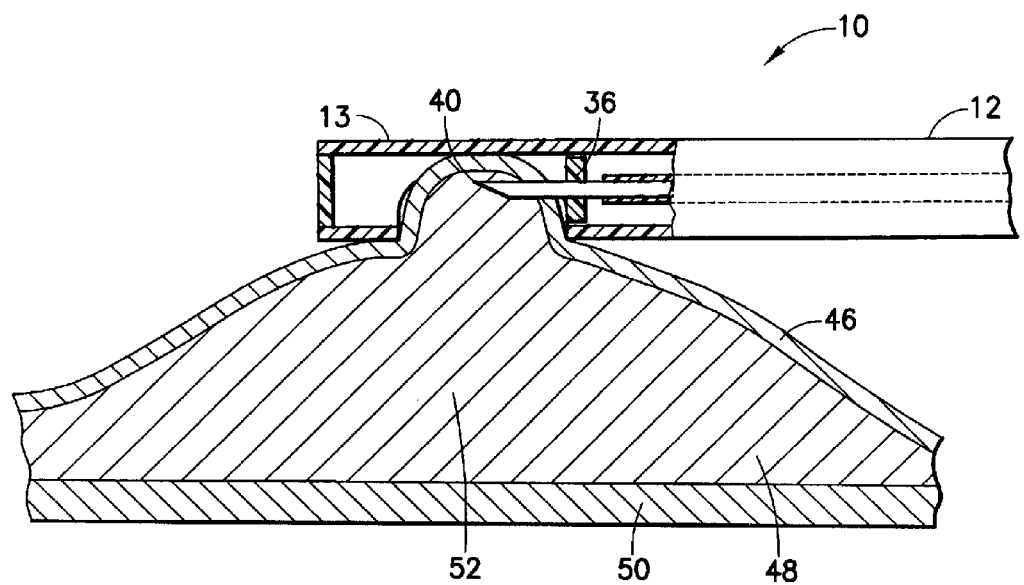
Figure 6E:
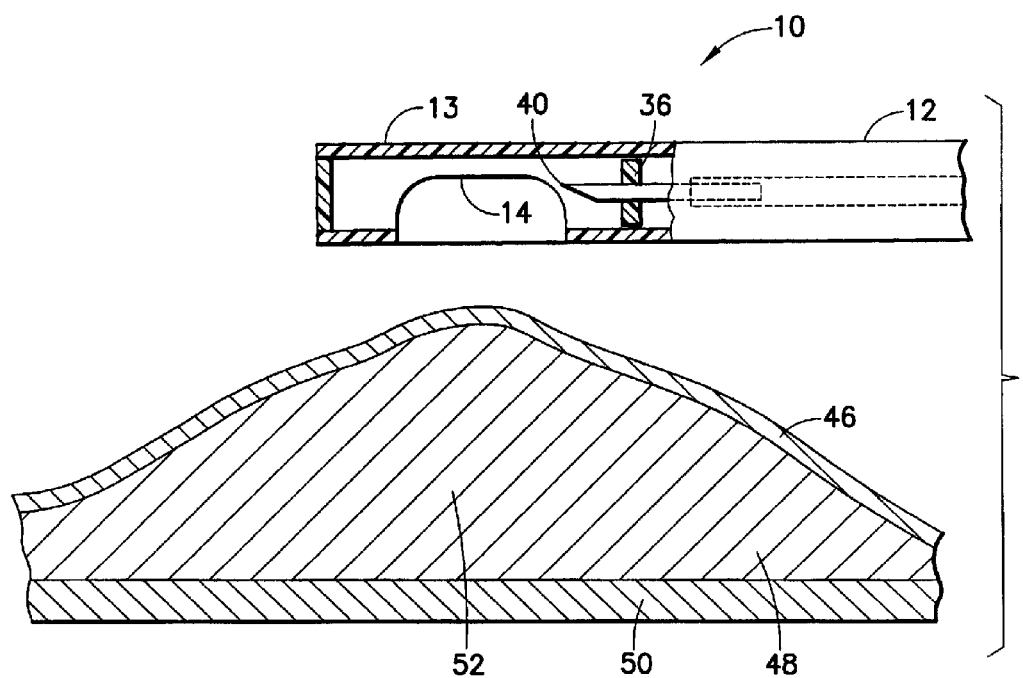

FIGS. 6A through 6E illustrate the operation of safe access needle injection instrument 10. Insertion section 6 of endoscope 2 is passed through a natural orifice in a patient and positioned at a location in the digestive tract in which to perform a submucosal procedure. Safe access needle injection instrument 10 is deployed through the working channel 4 of endoscope 2. As depicted in FIG. 6A the distal potion of safe access needle injection instrument 10 is positioned within the digestive tract adjacent mucosal layer 46. Beneath the mucosal layer are the submucosal layer 48 and the muscular layer 50. Window member 14 is oriented towards mucosal layer 46. Needle member 16 is located in a first position proximal to window member 14. A vacuum source is connected to vacuum port 18, which communicates with lumen 34, and the applied vacuum causes the tissue of the digestive tract to be suctioned into window member 14 as shown in FIG. 6B. The actuation of needle member 16 is shown in FIG. 6C as it is moved to its second position. Distal movement of needle member 16 causes needle tip 40 to move distally relative to tubular shaft 12 to thereby pierce the mucosal layer 46 and enter the submucosal layer 48 of the suctioned tissue. When needle member 16 is moved to its second position, stop member 36 engages the mucosal layer 46. Stop member 36 prevents further distal movement of needle member 16 and provides a seal around needle tip 40. A pressurized fluid source is connected to needle fluid port 24 to deliver fluid through the lumen of needle member 16 to the submucosal layer 48. As fluid enters the submucosal layer 48 from needle tip 40, as illustrated in FIG. 6D, the mucosal layer 46 is elevated forming a submucosal bleb. The fluid used to create the bleb may be of any type suitable for the environment such as solutions containing saline, hypertonic solutions of saline-epinephrine, sodium hyaluronate, poly-N-acetylglucosamine, sodium chondroitin sulfate, chitosans or other biocompatible mucopolysaccharides. Although the mucosal layer 46 is elevated to form the submucosal bleb, the submucosal connective tissue 52 is only stretched and not broken by the infusion of fluid into submucosal layer 48. Once the needle member 16 is returned to its first position and the applied vacuum to lumen 34 is discontinued, the safe access needle injection instrument 10 may be removed from the safety bleb as illustrated in FIG. 6E.

Figure 7A:
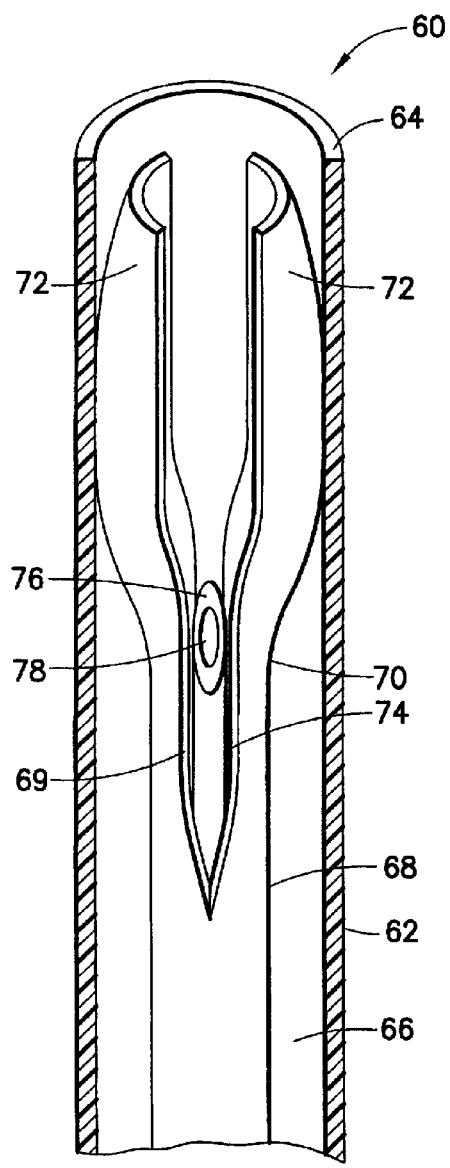
FIGS. 7A through 7C are partial cross-sectional views of a safe access needle injection instrument according to another embodiment of a submucosal medical procedure system of the present invention.
Figure 7B:
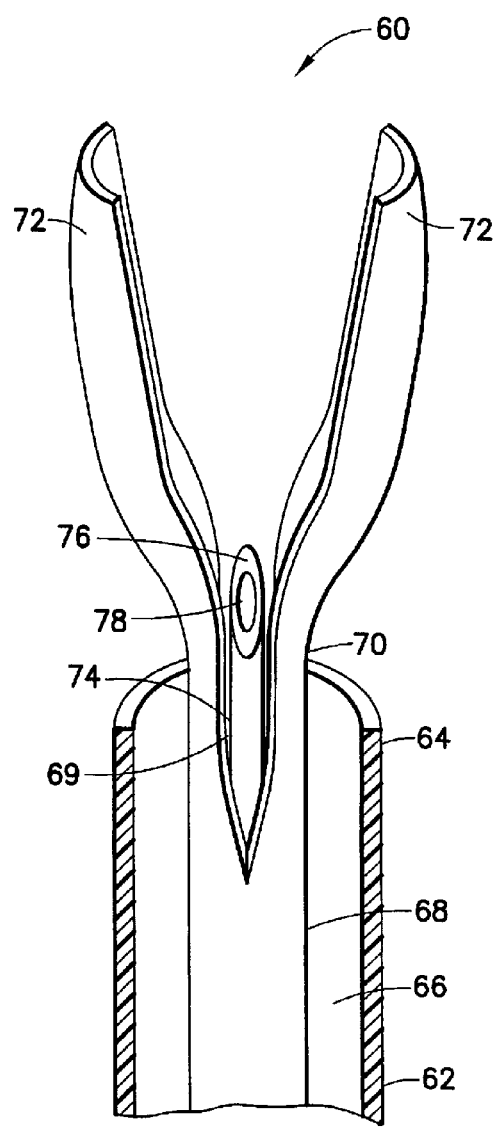
Figure 7C:
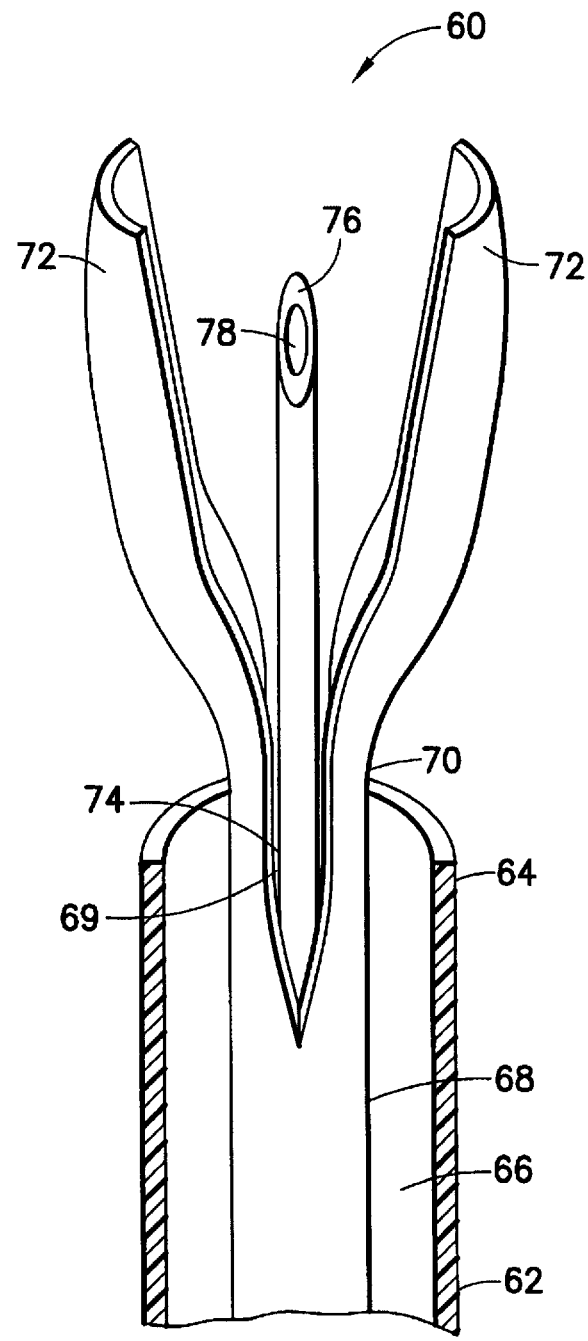

FIGS. 7A through 7C illustrate safe access needle injection instrument 60 which is another preferred embodiment of the present invention to aid the physician in obtaining access to the submucosal space when performing a submucosal medical procedure. Safe access needle injection instrument 60 includes a sheath member 62 having a proximal and distal end 64 and a lumen 66 extending therethrough. Slidably disposed within lumen 66 of sheath member 62, there is an elongate shaft member 68 having a shaft lumen 69 and distal end 70. Located adjacent to distal end 70 of elongated shaft member 68 is a pair of jaw members 72. Jaw members 72 may be formed from the wall of elongated shaft member 68. Preferably the jaw members 72 are formed of a resilient material and biased outwardly in an open configuration when unconstrained. The jaw members 72 may be formed from biocompatible resilient materials such as nitinol, stainless steel and plastics. Needle shaft 74 is slidably disposed within lumen 66 and preferably slidably disposed shaft lumen 69. Needle shaft 74 includes a needle tip 76 and a needle lumen 78. Needle lumen 78 extends from the proximal end of needle shaft 74 to needle tip 76. FIG. 7A illustrates jaw members 72 in a first state in which jaw members 72 are closed and constrained by the walls of sheath member 62 and disposed within lumen 66. Additionally, needle tip 78 of needle shaft 74 is in a first configuration in which needle tip 78 is positioned proximal to jaw members 72. By moving the elongate shaft member 68 distally relative to sheath member 62, jaw members 72 are caused to exit the lumen 66 at distal end 64 of sheath 62. FIG. 7B shows jaw members 72 in a second state in which in which the jaw members 72 are open and unconstrained after exiting lumen 66. FIG. 7C illustrates needle tip 78 of needle shaft 74 positioned in a second configuration in which needle tip 78 is positioned between jaw members 72.

Figure 8A:
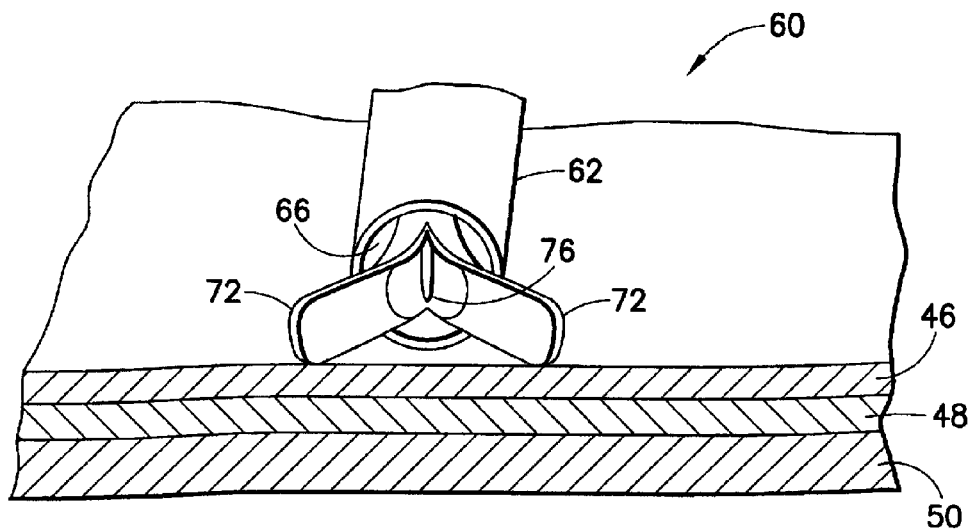
FIGS. 8A through 8E are cross sectional views showing a method creating a submucosal bleb using the safe access needle injection instrument according to another embodiment of present invention.
Figure 8B:
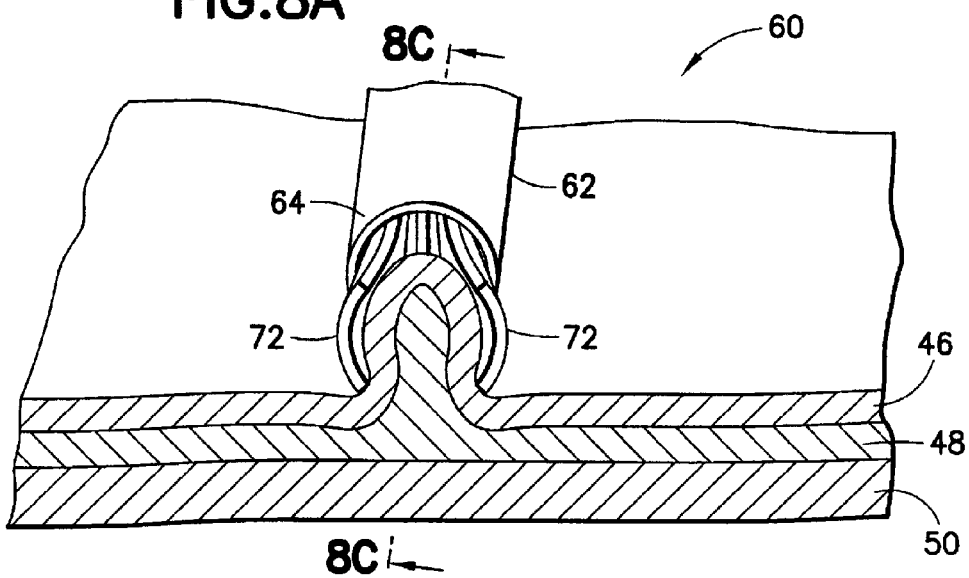
Figure 8C:
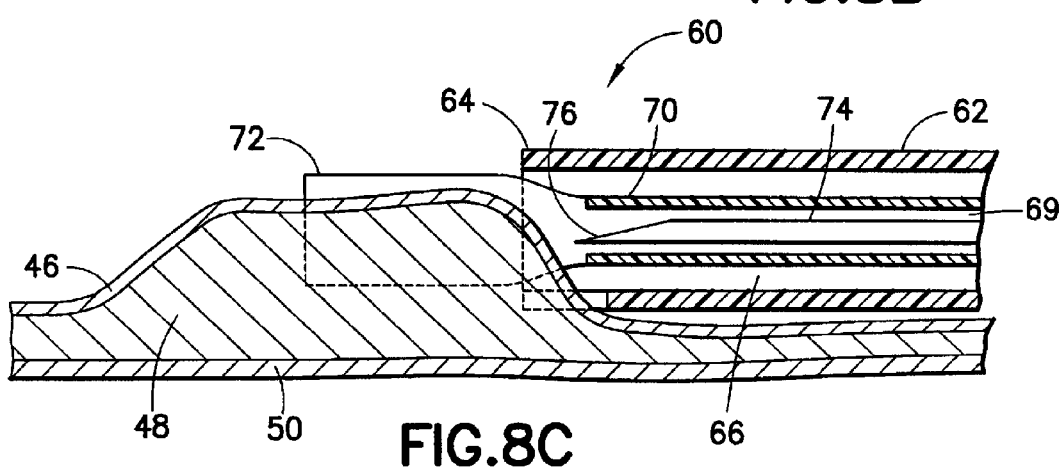
Figure 8D:
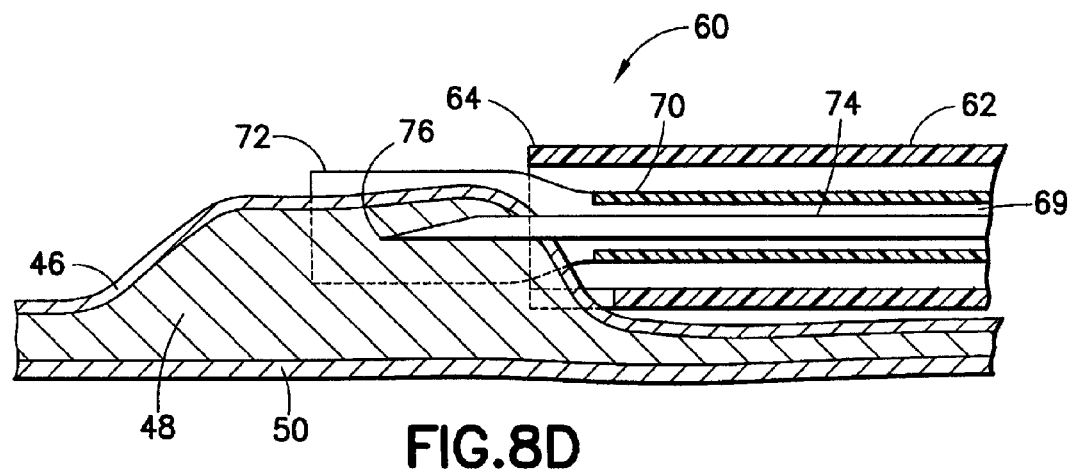
Figure 8E:
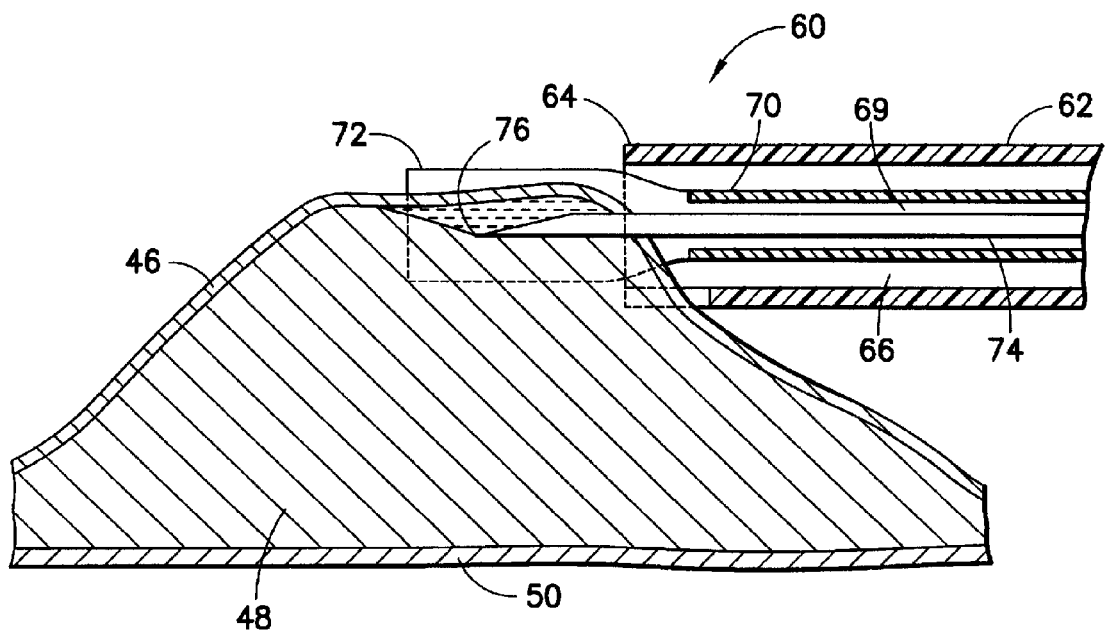

FIGS. 8A through 8E illustrates the operation of safe access needle injection instrument 60. Insertion section 6 of endoscope 2 is passed through a natural orifice in a patient and positioned at a location in the digestive tract in which to perform a submucosal procedure. Safe access needle injection instrument 60 is deployed through the working channel 4 of endoscope 2. As depicted in FIG. 8A the distal potion of safe access needle injection instrument 60 is positioned within the digestive tract adjacent mucosal layer 46. Beneath the mucosal layer are the submucosal layer 48 and the muscular layer 50. Jaw members 72 are positioned on mucosal layer 46. Needle tip 76 is located in a first position proximal to jaw members 72. Distal movement of sheath member 62 relative to the elongate shaft member causes the jaw members 72 to become partially constrained in lumen 66 and move towards a closed position thereby grasping the tissue of the digestive tract as shown in FIG. 8B. FIG. 8C is a cross-section view along section line 8C-8C in FIG. 8B showing the tissue engaged by jaw members 72. The mucosal layer 46 and submucosal layer 48 are firmly held between jaw members 72. Needle tip 76 is moved from the first position proximal to jaw members 72 to the second position between jaw members 72 thereby piercing the mucosal layer 46 and entering the submucosal layer 48 as shown in FIG. 8D. FIG. 8E illustrates the delivery of fluid through needle shaft 74 exiting needle tip 76 into the submucosal layer 48 thereby elevating mucosal layer 46 to form a submucosal bleb. The fluid used to create the bleb may be of any type suitable for the environment such as solutions containing saline, hypertonic solutions of saline-epinephrine, sodium hyaluronate, poly-N-acetylglucosamine, sodium chondroitin sulfate, chitosans or other biocompatible mucopolysaccharides.

Figure 9:
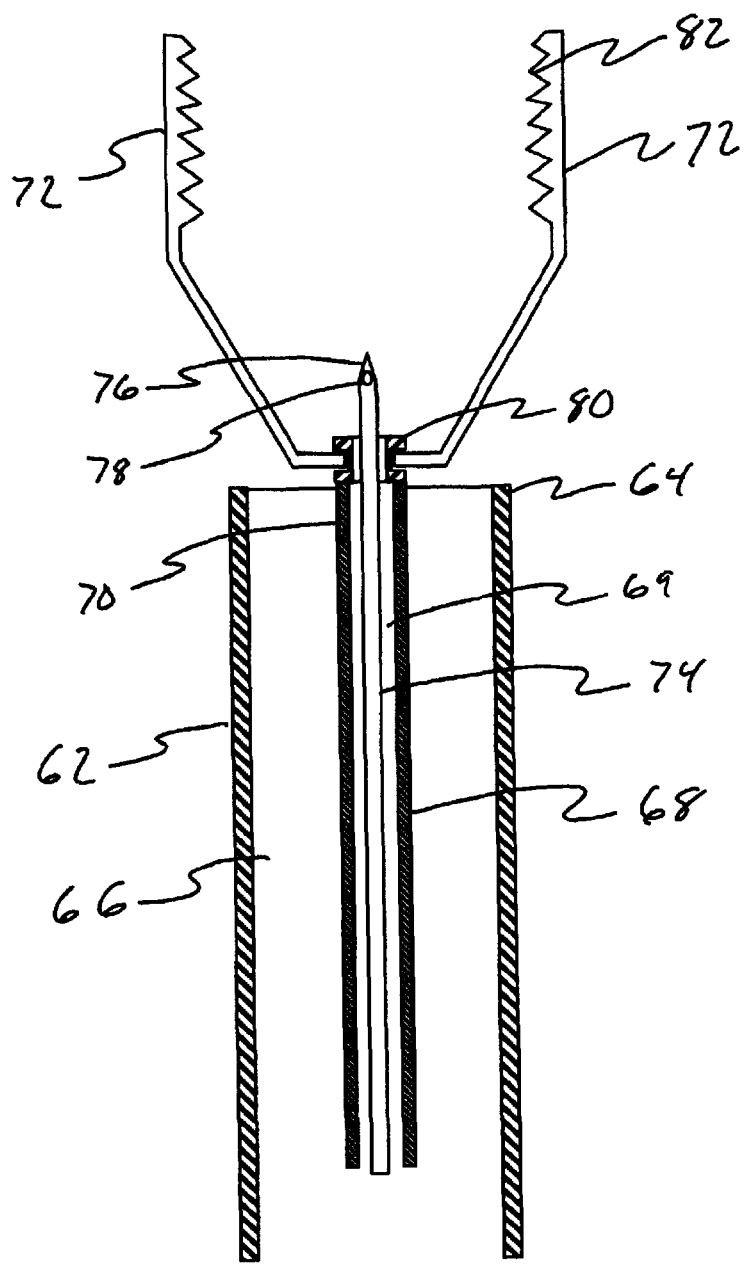
FIG. 9 is partial cross-sectional view of a safe access needle injection instrument according to another embodiment of the present invention.
Figure 10:
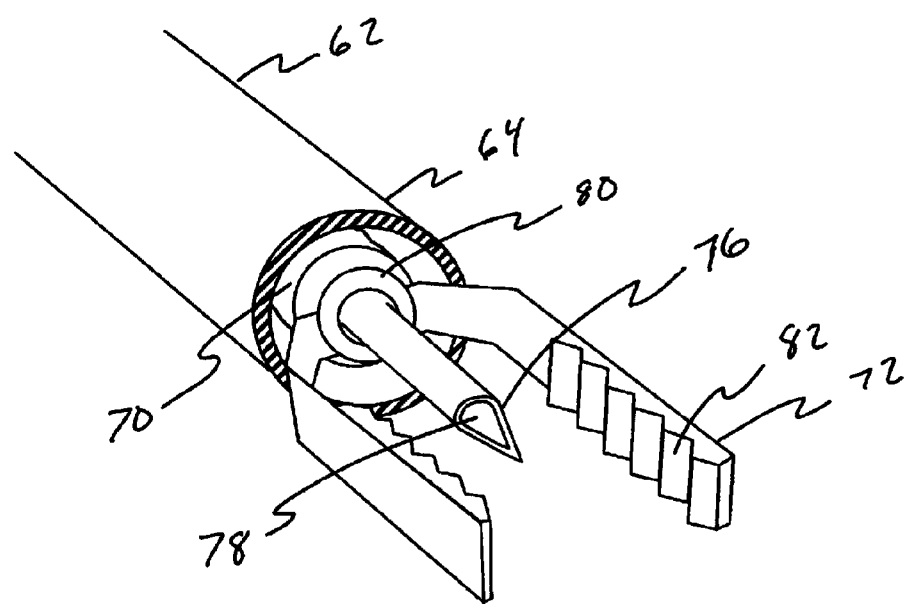
FIG. 10 is a perspective view of a safe access needle injection instrument according to another embodiment of the present invention.

FIGS. 9 and 10 show a variation of safe access needle injection instrument 60 in which jaw members 72 are coupled to distal end 70 of elongate shaft member 68 by a collar member 80. Collar member 80 is joined to distal end 70 by suitable means known in the art such as gluing, soldering or welding. Jaw members 72 are connected to collar member 80 in a way that allows the jaw members 72 to rotate relative to distal end 70 of elongate shaft member 68. The rotational movement of jaw members 72 allows the physician to quickly orient the jaw members 72 relative the surface of the tissue surface within the digestive tract. Although jaw members 72 are connected to collar member 80, proximal movement of elongate shaft member 68 relative to sheath member 62 will cause jaw members 72 to move to a closed position within the lumen 66 of sheath member 62. Collar member 80 includes an aperture through which needle shaft 74 may extend in a slidable fashion. Additionally, jaw members 72 include a tissue grasping surface 82 that facilitates the engagement of tissue within the digestive tract. While tissue grasping surface 82 is shown in the form of a serrated surface, it may also take the form of a knurled surface or a surface containing multiple protrusions or dimples to improve the tissue grasping ability of jaw members 72. Tissue grasping surface 82 may be integrally formed with jaw members 72 or bonded to jaw members 72. Tissue grasping surface 82 may be formed of metals, polymers or composite materials.

Figure 11A:
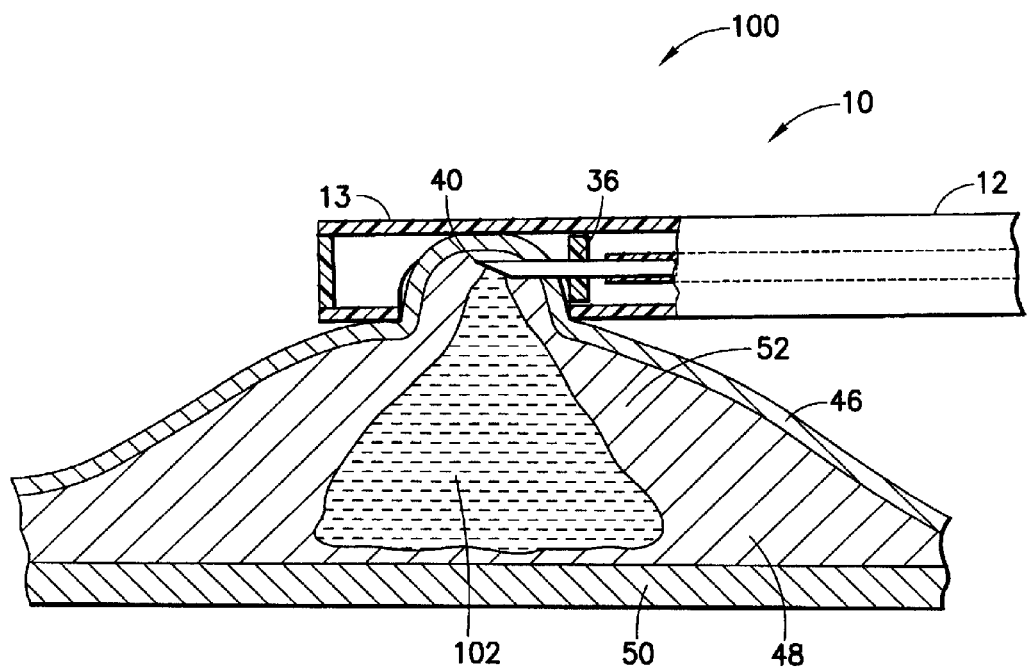
FIGS. 11A and 11B are cross-sectional views showing a method for dissecting a submucosal layer according to an embodiment of the present invention.
Figure 11B:
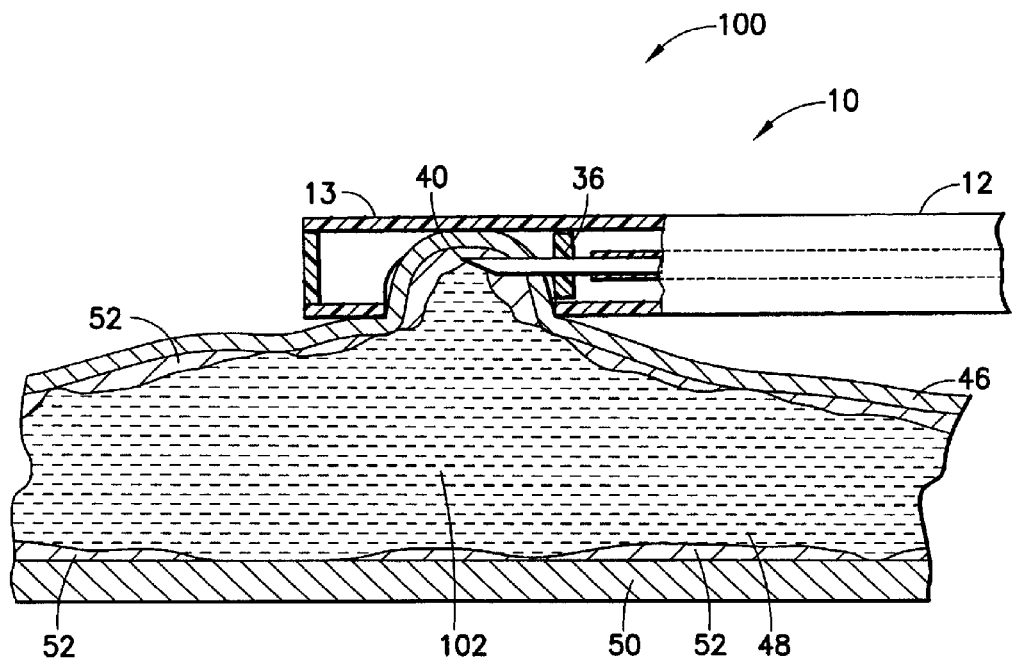

FIGS. 11A and 11B show a safe access dissection system 100 of the present invention that includes a safe access needle injection instrument 10 and an injectable dissection material 102. The injectable dissection material 102 takes the form of a solution capable of dissolving the submucosal connective tissue. An example of this type of dissolving solution is sodium 2-mercaptoethanesulfanate (MESNA). Additional substances which may dissolve the submucosal connective tissue include acids and enzymes such as a peptase enzyme solution, protease/collagenase, papain, chymotrypsin and acetylcysteine. A safe access needle injection instrument 10 is used to create a safety bleb beneath the mucosal layer 46 in the digestive tract of a mammal. Once the safety bleb is formed, the injectable dissection material 102 may be delivered through needle tip 40 into the submucosal layer 48 as shown in FIG. 11A. Injectable dissection material 102 begins to breakdown the stretched submucosal connective tissue 52. Under the force imparted by the distention of the bleb, the submucosal connective tissue 52 breaks, thereby causing the mucosal layer 46 to become detached from muscular layer 50 in bleb region as shown in FIG. 11B.

Figure 12A:
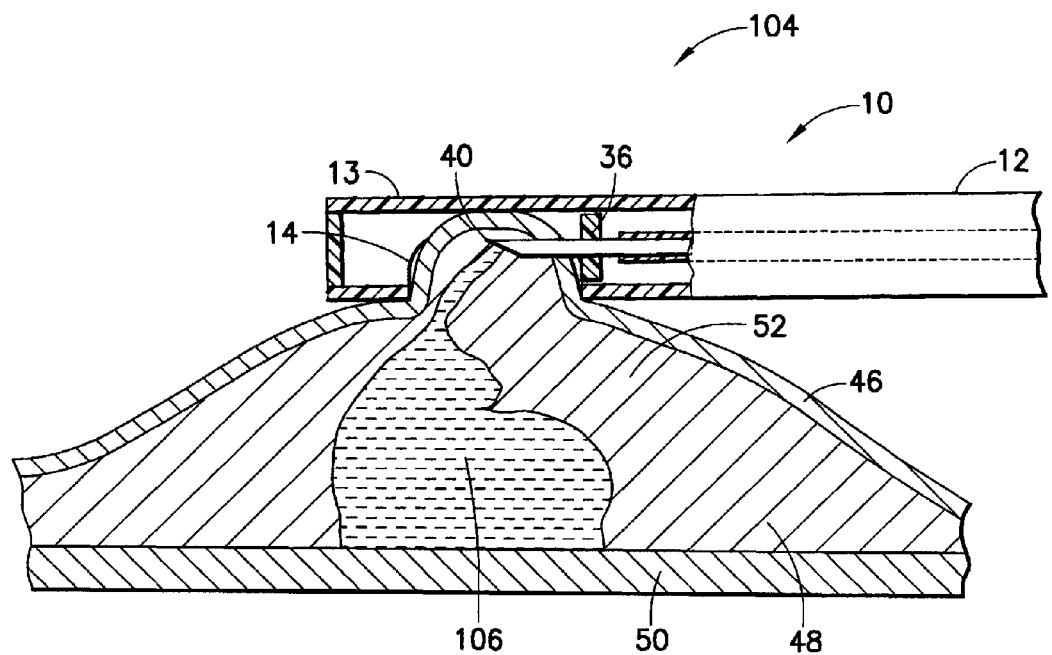
FIGS. 12A and 12B are cross-sectional views showing a method for dissecting a submucosal layer according to another embodiment of the present invention.
Figure 12B:
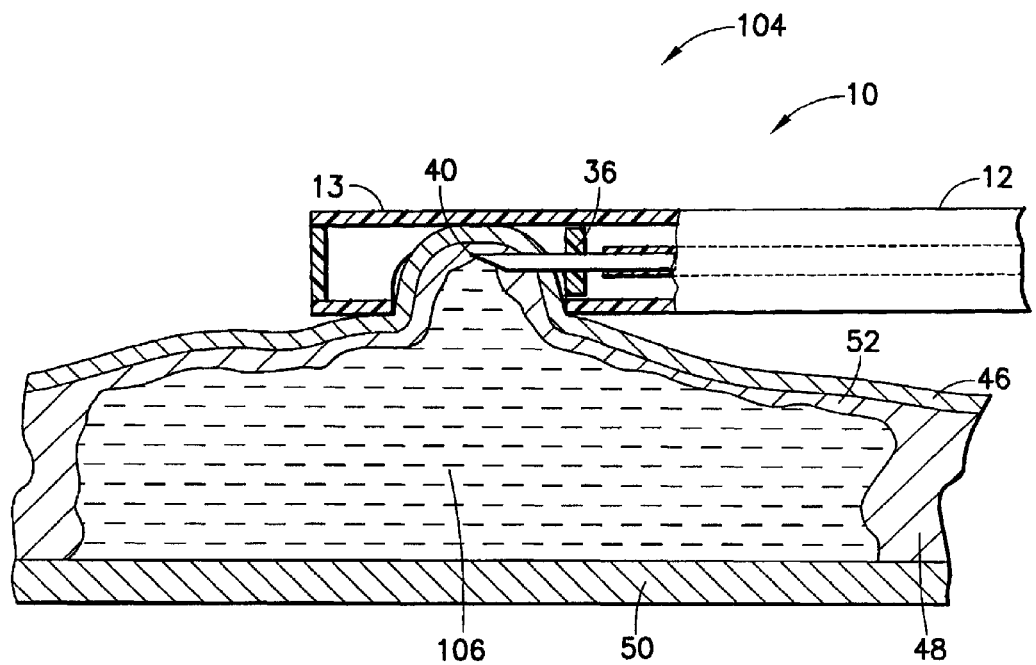

FIGS. 12A and 12B show a safe access dissection system 104 of the present invention that includes a safe access needle injection instrument 10 and an injectable dissection material 106. The injectable dissection material 106 takes the form of a semisolid gelatin capable of mechanically breaking the submucosal connective tissue 52. The semisolid gelatin may be formed using biocompatible commercially available gelatins. Generally, these gelatins are in a powdered form and mixed with warm water. Upon cooling, the gelatin forms a semisolid consistency with physical cross links. The gelatin material is preferably formed within the barrel of a pressurizable syringe since aspiration of this material is difficult. A safe access needle injection instrument 10 is used to create a safety bleb beneath the mucosal layer 46 in the digestive tract of a mammal. Once the safety bleb is formed, the injectable dissection material 106 may be delivered through needle tip 40 into the submucosal layer 48 as shown in FIG. 12A. The mass and semisolid nature of the injectable dissection material 106 begins to apply force to the stretched submucosal connective tissue 52, unlike a saline solution which only permeates the submucosal layer 48. Under the force imparted by the increased volume due to the introduction of the injectable dissection material 106, the submucosal connective tissue 52 breaks, thereby causing the mucosal layer 46 to become detached from muscular layer 50 in bleb region as shown in FIG. 12B. Alternatively, the injectable dissection material 106 may also take the form of injectable solutions which solidify upon entering the submucosal space. Solutions which solidify after injection into the submucosal space may be thermo sensitive polymer solutions such as Pluronic 127. Additional injectable solidifying solutions include monomer and polymer solutions like hydrogels and cyanoacrylates which polymerize or crosslink upon contact with tissue or added chemical agents.

Figure 13A:
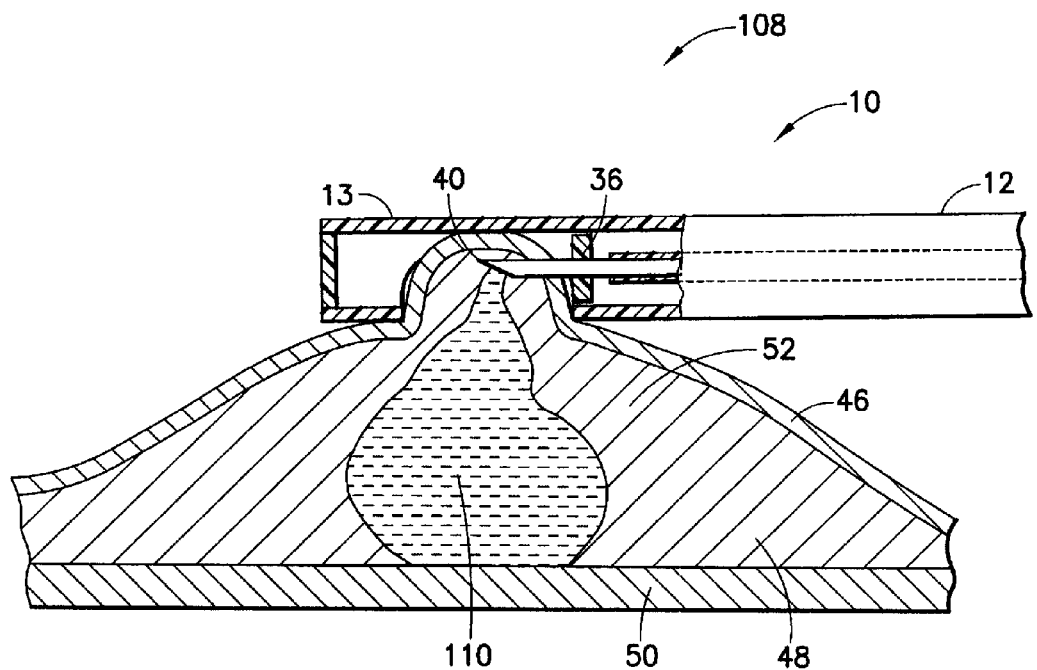
FIGS. 13A and 13B are cross-sectional views showing a method for dissecting a submucosal layer according to yet another embodiment of the present invention.
Figure 13B:
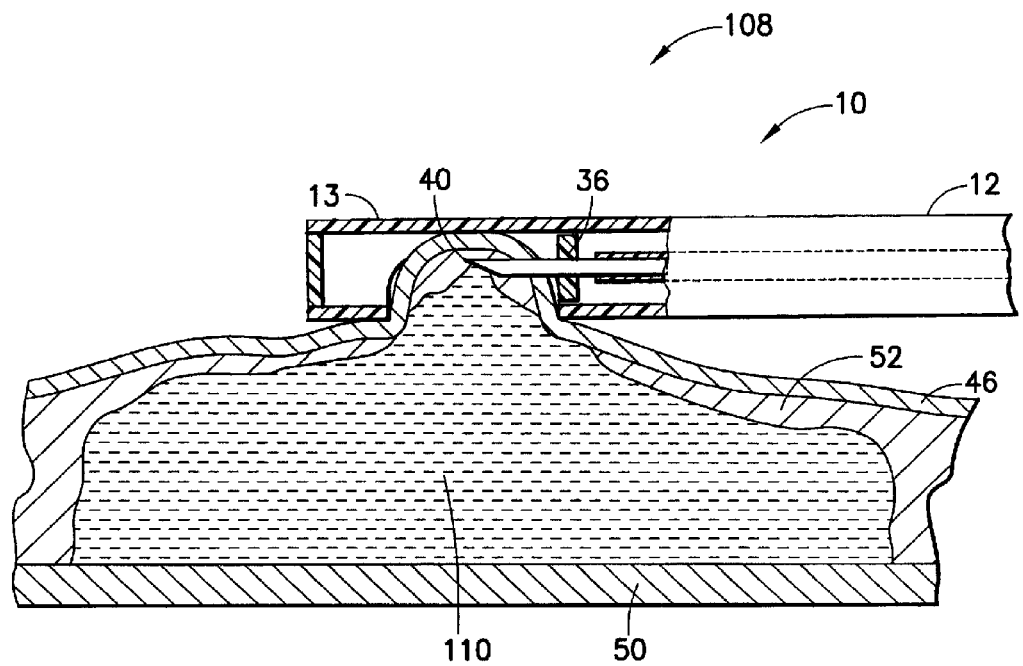

FIGS. 13A and 13B show a safe access dissection system 108 of the present invention that includes a safe access needle injection instrument 10 and an injectable dissection material 110. The injectable dissection material 110 takes the form of gelled microspheres dispersed in a solution capable of mechanically breaking the submucosal connective tissue 52. The microspheres may be formed using biocompatible natural materials such as collagen and alginates or synthetic materials like polyvinylalcohol (PVA), polyvinylpyrolidone (PVP) and acrylate polymers. A safe access needle injection instrument 10 is used to create a safety bleb beneath the mucosal layer 46 in the digestive tract of a mammal. Once the safety bleb is formed, the injectable dissection material 110 may be delivered through needle tip 40 into the submucosal layer 48 as shown in FIG. 13A. The mass and solid nature of the injectable dissection material 110 begins to apply force to the stretched submucosal connective tissue 52, unlike a saline solution which only permeates the submucosal layer 48. Under the force imparted by the increased volume due to the introduction of the injectable dissection material 110, the submucosal connective tissue 52 breaks, thereby causing the mucosal layer 46 to become detached from muscular layer 50 in bleb region as shown in FIG. 13B.

Figure 14:
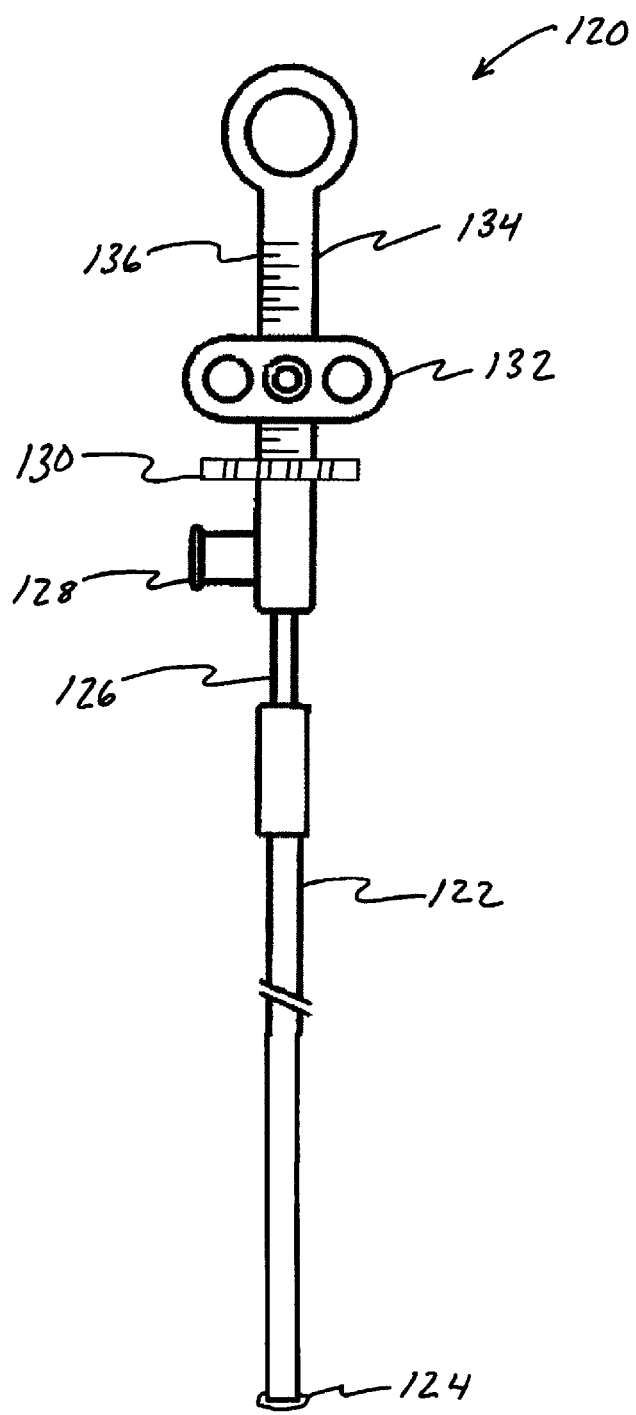
FIG. 14 is a side view showing a submucosal tunneling instrument of a submucosal medical procedure system in accordance with an embodiment of the present invention.

FIG. 14 illustrates a submucosal tunneling instrument 120 for performing a submucosal medical procedure of the present invention. The submucosal tunneling instrument 120 includes a catheter 122 having proximal and distal ends and a balloon member 124 located adjacent the distal end. The proximal end of catheter 122 is attached to connector tubing 126 to access inflation port 128. Valve assembly 130 provides a seal for fluid introduced into inflation port 128. Tether slide 132 is slidably positioned on handle body 134. Handle body 134 includes distance markers 136 to gauge the movement of tether slide 132.

Figures 15A, 15B:
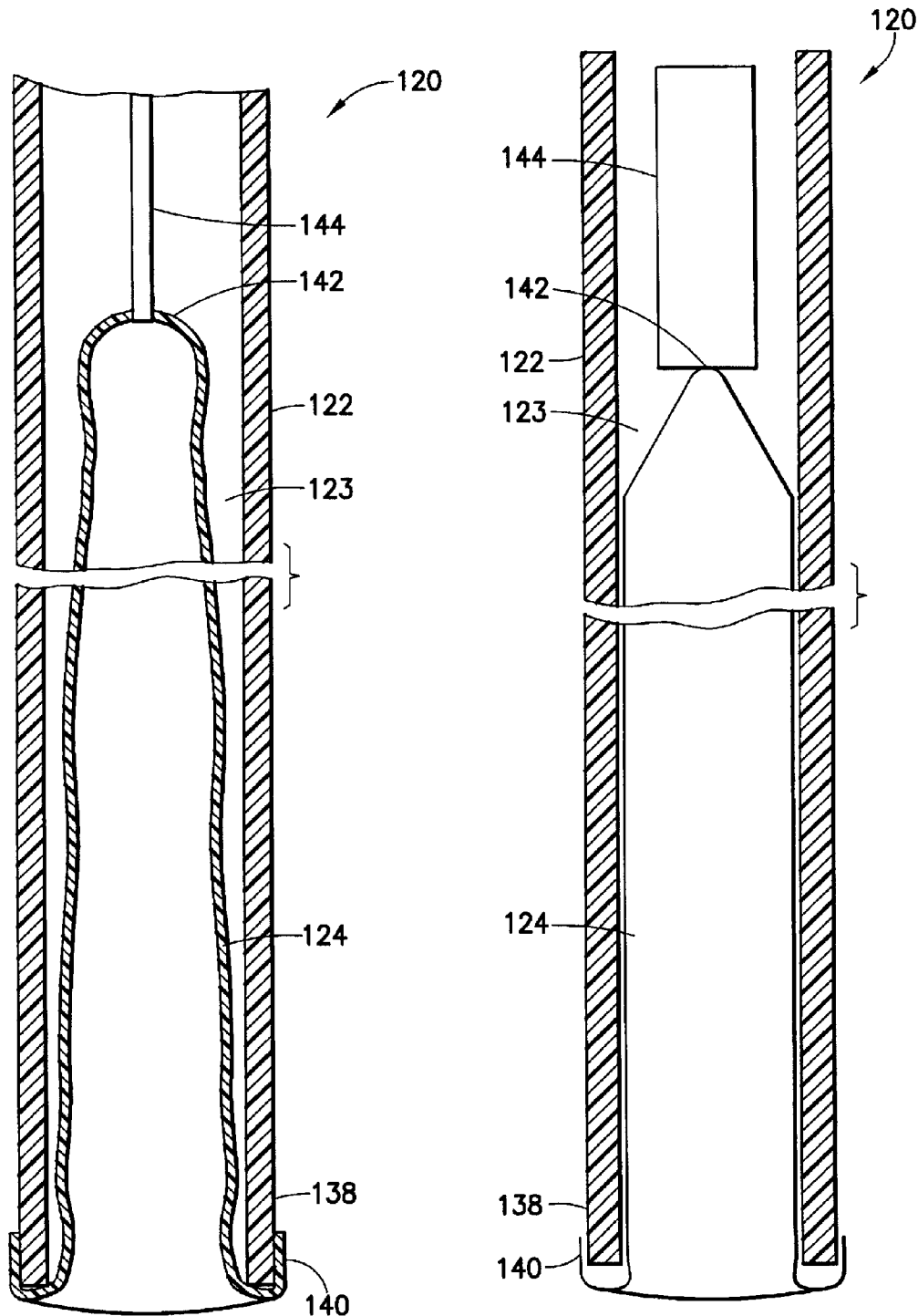
FIGS. 15A and B are a cross-sectional views showing a submucosal tunneling instrument of a submucosal medical procedure system in accordance with an embodiment of the present invention.

A cross sectioned view of the distal end of the submucosal tunneling instrument 120 is shown in more detail in FIG. 15. Catheter 122 has a distal end 138 and a lumen 123. Located within lumen 123 is balloon member 124. The balloon member 124 is preferably noncompliant of the type generally known in the art, however, balloon member 124 may be of the compliant or semi-compliant type. The balloon member 124 may be formed from biocompatible polymer types such as olefins, elastomers, thermoplastic elastomers, vinyls, polyamides, polyimides, polyesters, fluropolymers, copolymers and blends of any of the aforementioned. The proximal end 140 of balloon member 124 is attached to the distal end 138 of catheter 122. The distal end 142 of balloon member 124 is positioned within the lumen 123 in an everted configuration. A tether member 144 is connected to the distal end 142 of balloon member 124. Tether member 144 is flexible and preferably takes the form of a filament, as shown, however tether member 144 may take the form of a tube. The proximal end of tether member 144 is connected to tether slide 132 through valve assembly 130. Tether member 144 aids in initially positioning balloon member 124 within the lumen 123 of catheter 122. While the aforementioned embodiment of the submucosal tunneling instrument include an expandable member which preferably takes the form of an inflatable balloon, other devices may be suitable for essentially performing the same function. For instance as depicted in an alternate embodiment shown in FIG. 15B, the expandable member 124 may take the form of an expandable elongate braid, mesh or tubular framework in which the proximal end of the expandable member is connected to the distal end of the catheter and the distal end of the expandable member is everted and positioned within the lumen of the catheter. A stiffened tether member 144 located within the lumen of the catheter 122 may be used as a pusher to push the expandable elongate member from the lumen of the catheter in essentially the same way that the balloon expands from the lumen of the catheter. The expandable elongate braid may be formed from resilient materials such as nitinol, spring steels, vitreloy, as well as polymers and composites. The expandable member may take comprise individual wires to form a braid or mesh configuration. Alternatively the expandable member may be laser cut from a tube forming a tubular framework. Preferably the expanded diameter is larger than the outer diameter of the catheter.

Figure 16A:
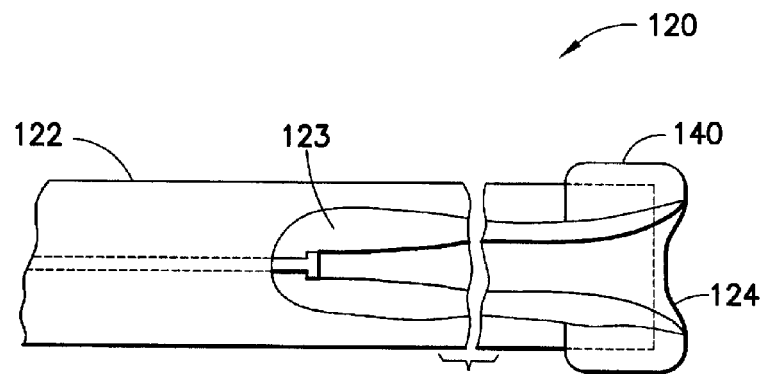
FIGS. 16A through 16C are partial cross-sectional views showing a sequence of expanding the distal end of a submucosal tunneling instrument of a submucosal medical procedure system in accordance with an embodiment of the present invention.
Figure 16B:
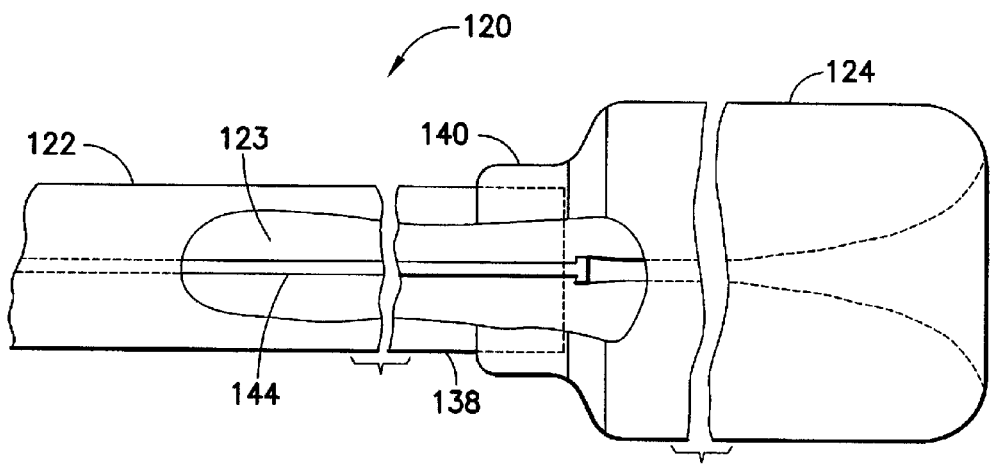
Figure 16C:
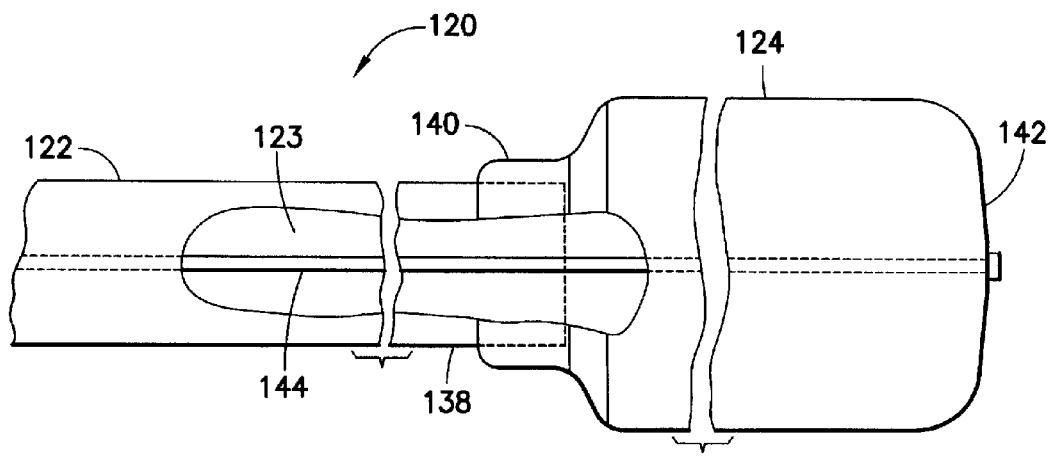

FIGS. 16A through 16C illustrate various stages of deployment of balloon member 124 from the lumen 123 of catheter 122. To deploy balloon member 124 a fluid filled syringe or other source is connected to inflation port 128. As pressurized fluid enters the lumen 123 of catheter 122, the proximal end of balloon member 124 exits the lumen expands. Balloon member 124 has an expanded diameter range of about 1 mm to about 30 mm and is preferably in the range of 2 mm to 20 mm. The length of balloon member 124 is a long as necessary to perform a desired submucosal medical procedure. This length can be in the range of 5 mm to 50 cm and preferably in the range of 7 mm to about 10 cm. As balloon member 124 expands it extends in a linear fashion moving the distal end 142 of balloon member 124 towards the distal end 138 of catheter 122. As long as pressurized fluid is applied to catheter lumen 123, balloon 124 will extend to its full length. Alternatively, since the distal end 142 of balloon 124 is connected to tether member 144, the amount of linear extension balloon 124 takes may be controlled by the tether slide 132 to define an extension length shorter than the full length of the balloon.

Figure 17:
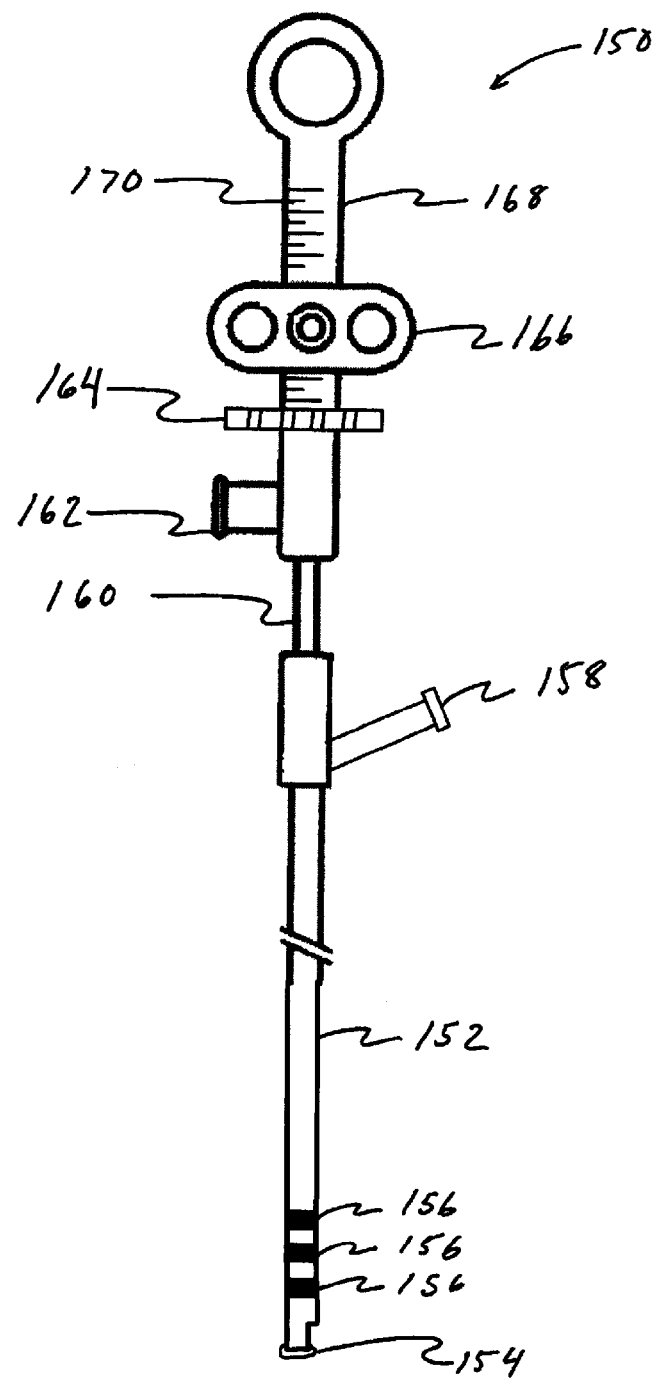
FIG. 17 is a side view showing a variation of a submucosal tunneling instrument of a submucosal medical procedure system in accordance with an embodiment of the present invention.

FIG. 17 illustrates a submucosal tunneling instrument 150 for performing a submucosal medical procedure of the present invention. The submucosal tunneling instrument 150 includes a catheter 152 having proximal and distal ends and a balloon member 154 located adjacent the distal end. Positioned on the exterior of catheter 152 adjacent the distal end is a series of markers 156. These markers may be visible under direct visualization of the endoscope and may be additionally visible under fluoroscopy. Adjacent the proximal end of catheter 152 is an auxiliary device port 158. The proximal end of catheter 152 is attached to connector tubing 160 to access inflation port 162. Valve assembly 164 provides a seal for fluid introduced into inflation port 162. Tether slide 166 is slidably positioned on handle body 168. Handle body 168 includes distance markers 170 to gauge the movement of tether slide 166.

Figure 18:
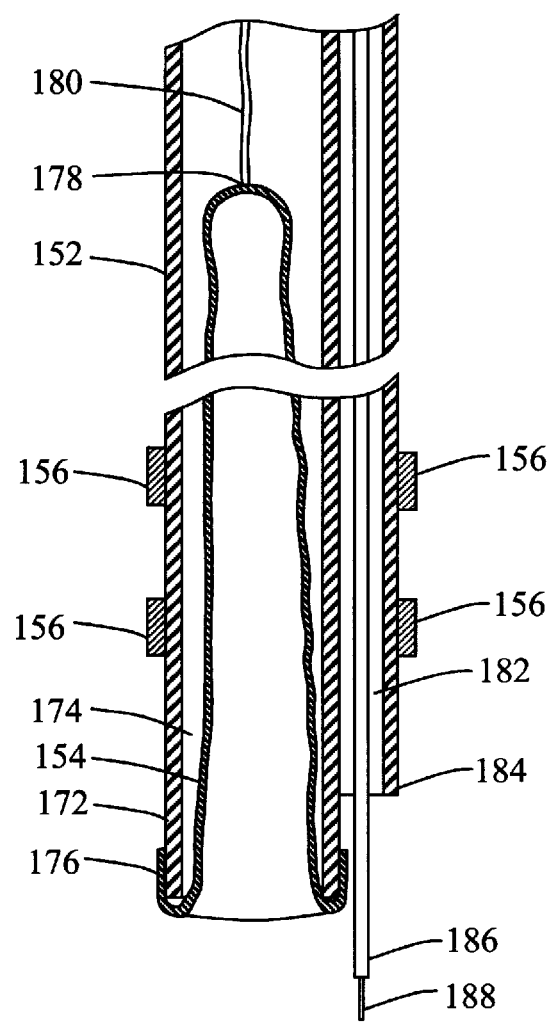
FIG. 18 is a cross-sectional view showing a sequence of expanding the distal end of another variation a submucosal tunneling instrument of a submucosal medical procedure system in accordance with an embodiment of the present invention.

A cross sectioned view of the distal end of the submucosal tunneling instrument 150 is shown in more detail in FIG. 18. Catheter 152 has a distal end 172 and a first lumen 174. Located within first lumen 174 is balloon member 154. The balloon member 154 is preferably non-compliant of the type generally known in the art, however, balloon member 154 may be of the compliant or semi-compliant type. The balloon member 154 may be formed from biocompatible polymer types such as olefins, elastomers, thermoplastic elastomers, vinyls, polyamides, polyimides, polyesters, fluropolymers, copolymers and blends of any of the aforementioned. The proximal end 176 of balloon member 154 is attached to the distal end 172 of catheter 152. The distal end 178 of balloon member 154 is positioned within the first lumen 174 in an everted configuration. A tether member 180 is connected to the distal end 178 of balloon member 154. Tether member 180 is flexible and preferably takes the form of a filament, as shown, however tether member 180 may take the form of a tube. The proximal end of tether member 180 is connected to tether slide 166 through valve assembly 164. Tether member 180 aids in initially positioning balloon member 154 within the first lumen 174 of catheter 152. Catheter 152 has a second lumen 182 that extends from auxiliary device port 158 to distal end 184. Distal end 184 is located proximal to distal end 172 of catheter 152. Slidably disposed within second lumen 182 is a needle knife 184 that has a knife tip 188. Needle knife 184 is preferably of the endoscopic electrosurgical type however any form of incision device that may be operated to form an incision in tissue such as mechanical cutters, water jets or lasers may be suitable.

Figure 19A:
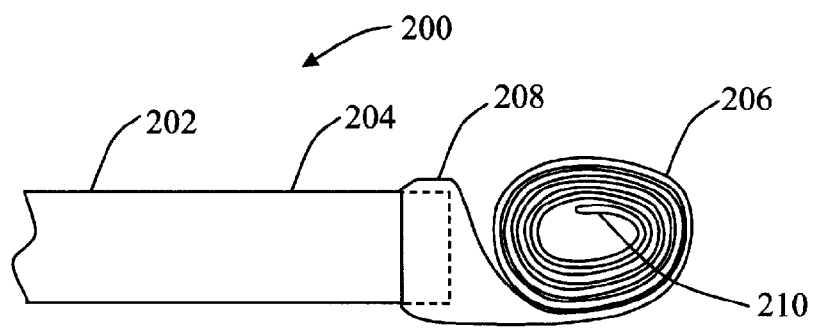
FIGS. 19A through 19C are a side views showing another variation of a submucosal tunneling instrument of a submucosal medical procedure system in accordance with an embodiment of the present invention.
Figure 19B:
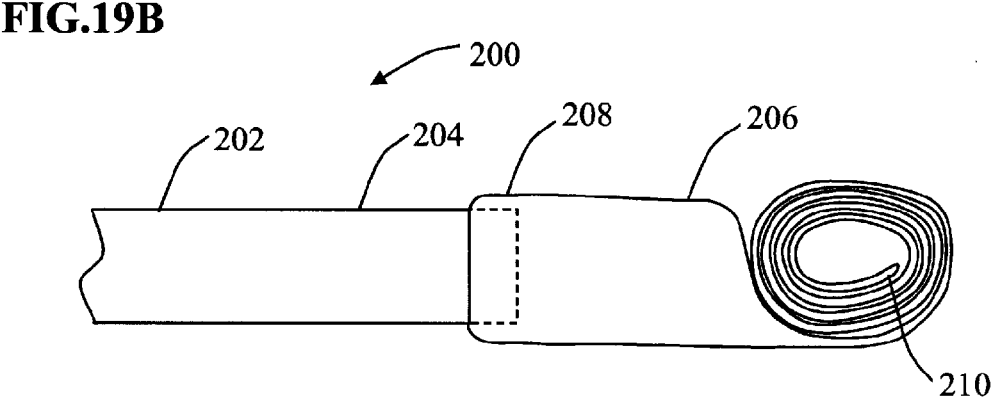
Figure 19C:
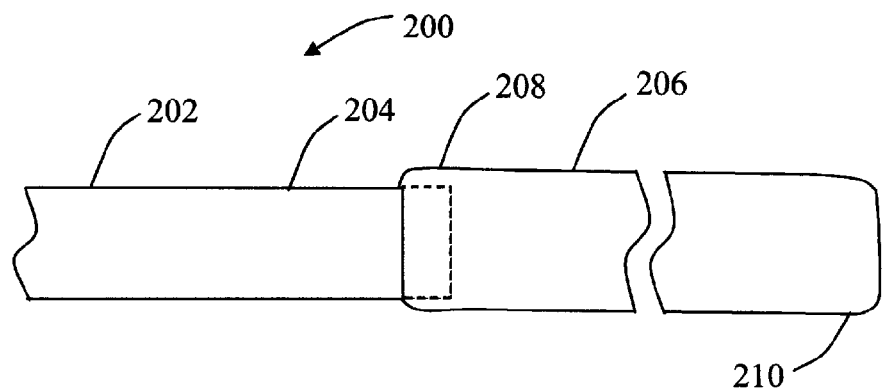
Figure 20A:
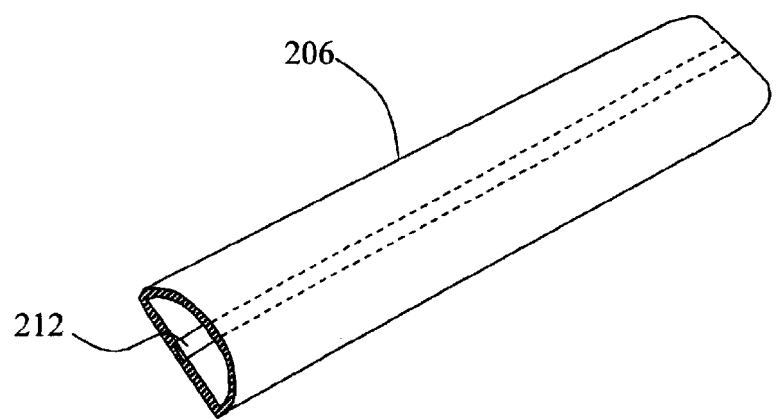
FIGS. 20A and 20B are perspective views showing a variation of the distal end of a submucosal tunneling instrument of a submucosal medical procedure system in accordance with an embodiment of the present invention.
Figure 20B:
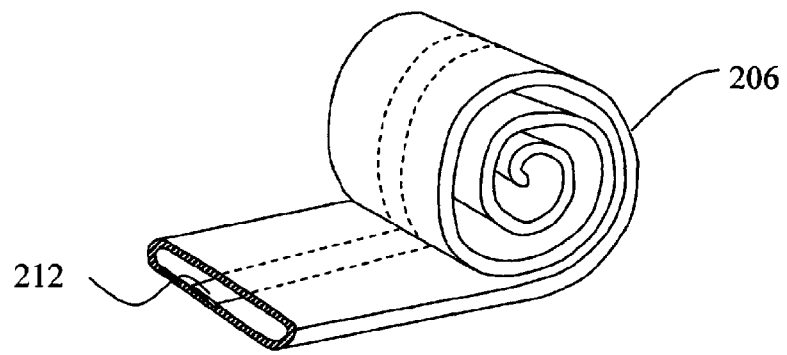

FIGS. 19A through 19C illustrate a submucosal tunneling instrument 200, according to another embodiment of the present invention. Catheter 202 has a distal end 204 which is connected to balloon member 206. The proximal end 208 of balloon 206 is connected to distal end 204 of catheter 202. Balloon member 206 is rolled into a spiral configuration in which the distal end 210 is located in the center of the spiral. As the lumen of catheter 202 which is connected to balloon member 206 is pressurized, balloon member 206 inflates. The inflation of balloon member 206 causes the balloon to unroll from a spiral configuration extending linearly. The balloon member 206 may be thermally treated to retain the spiral configuration for delivery through the working channel of an endoscope. Alternatively the balloon member 206 may incorporate a spiral shaped member 212 attached the wall of balloon member 206 as shown in FIGS. 20A and 20B. The spiral shaped member may be formed from a resilient filament as shown in an outstretched configuration in FIG. 20A. The spiral shaped member being formed of a resilient filament and incorporated into the wall of the balloon preferably takes its spiral shape and in doing so forms the balloon member into a spiral shape as shown in FIG. 20B.

Figure 21A:
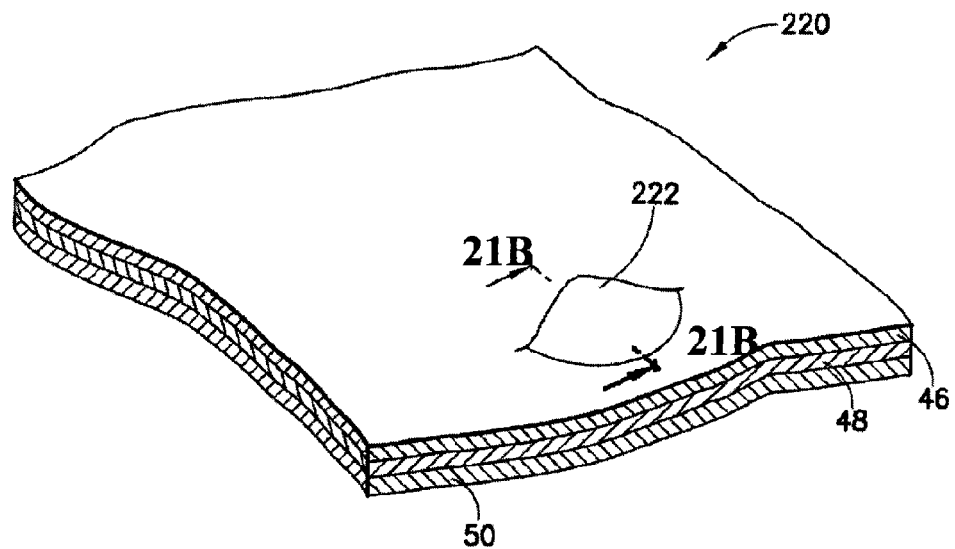
FIGS. 21A and 21B are perspective and cross sectional views of an area of tissue in the digestive tract having a submucosal saline bleb in accordance with an embodiment of the present invention.
Figure 21B:
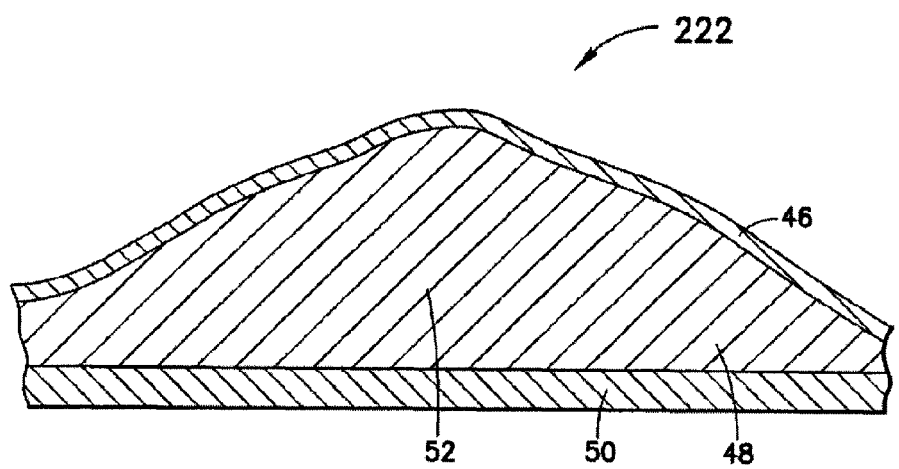
Figure 22A:
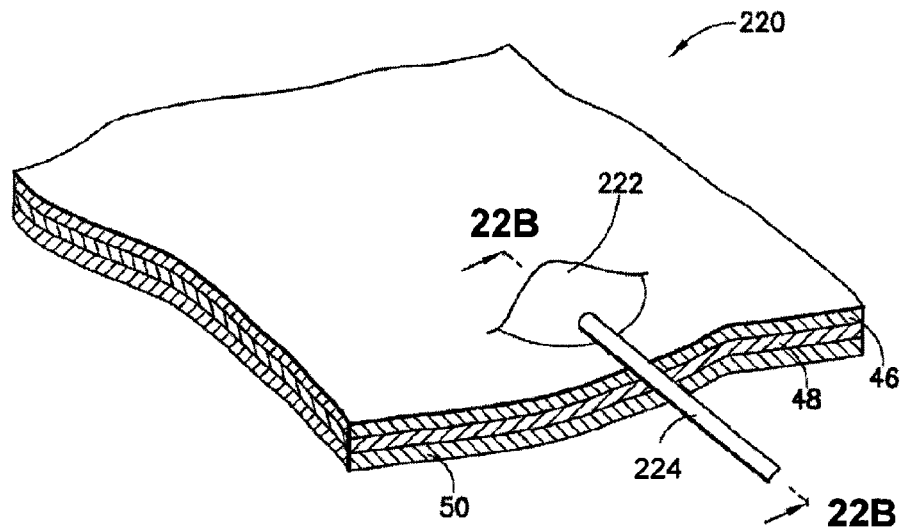
FIGS. 22A and 22B are perspective and cross sectional views of an area of tissue in the digestive tract having a submucosal saline bleb in which an opening through the mucosal layer is made in accordance with an embodiment of the present invention.
Figure 22B:
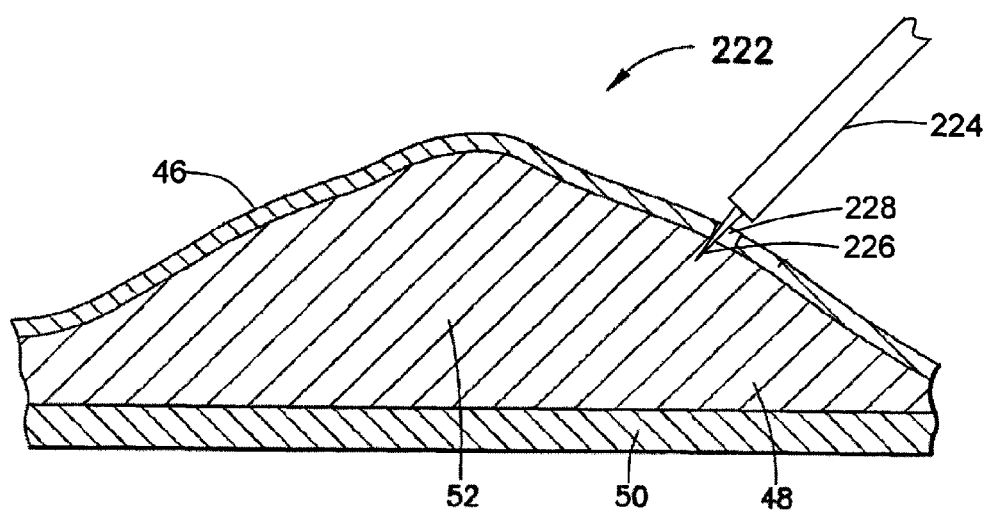
Figure 23A:
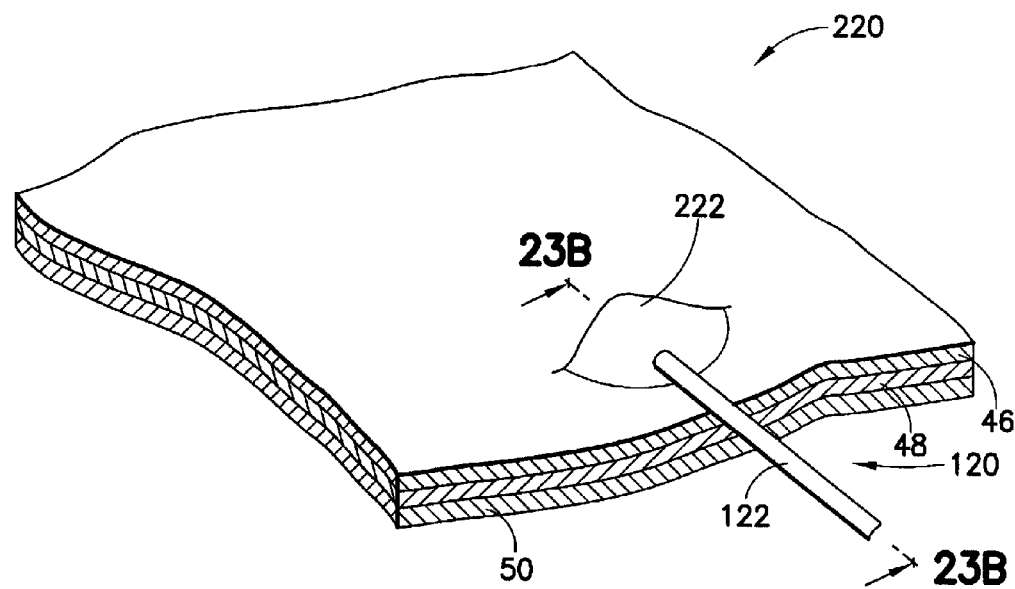
FIGS. 23A through 23D are perspective and cross sectional views showing a method of forming a submucosal tunnel using a submucosal tunneling instrument according to an embodiment of a submucosal medical procedure system of the present invention.
Figure 23B:
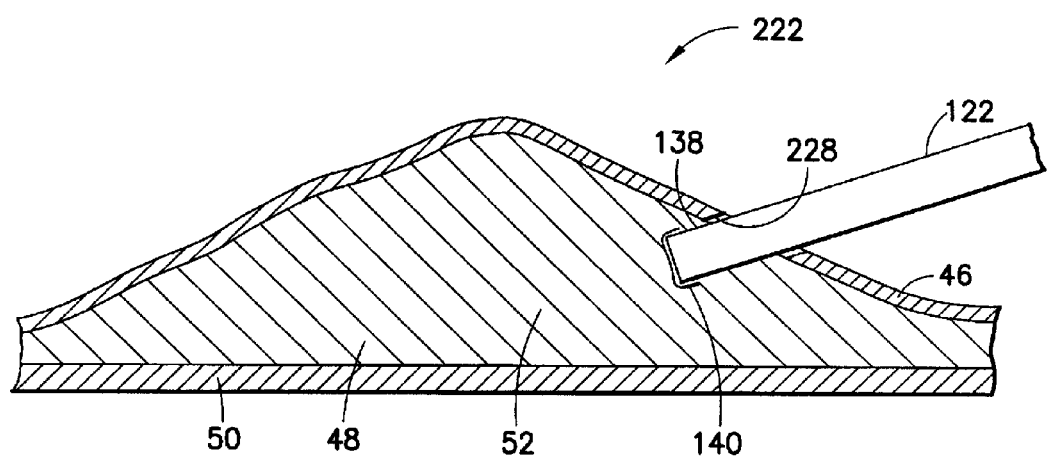
Figure 23C:
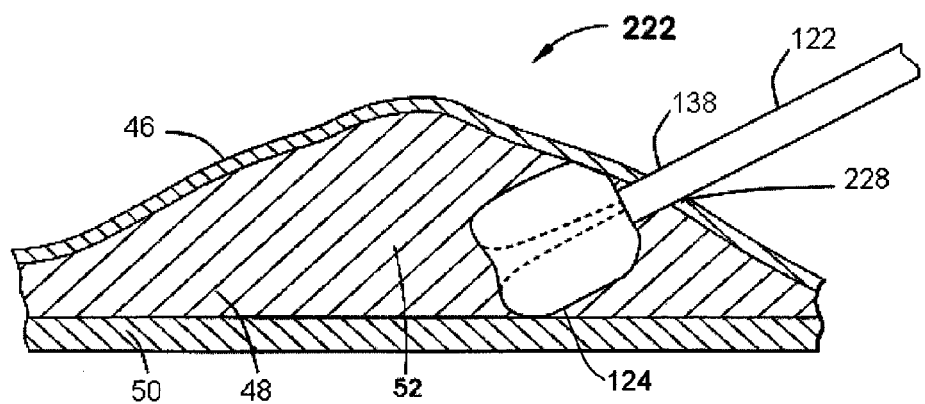
Figure 23D:
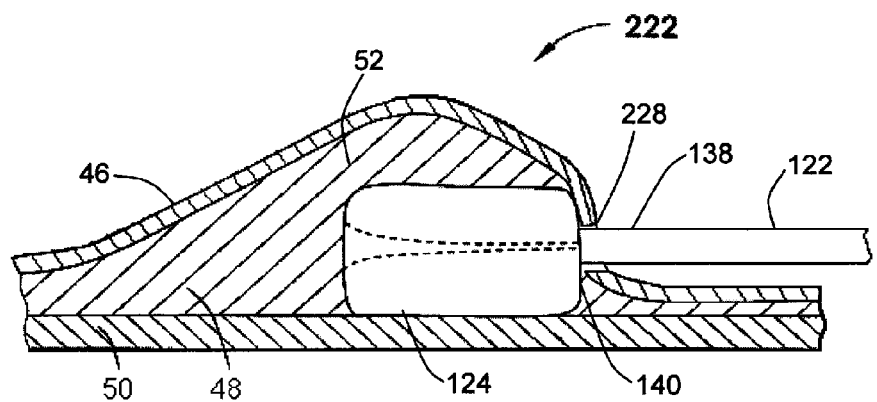
Figure 24A:
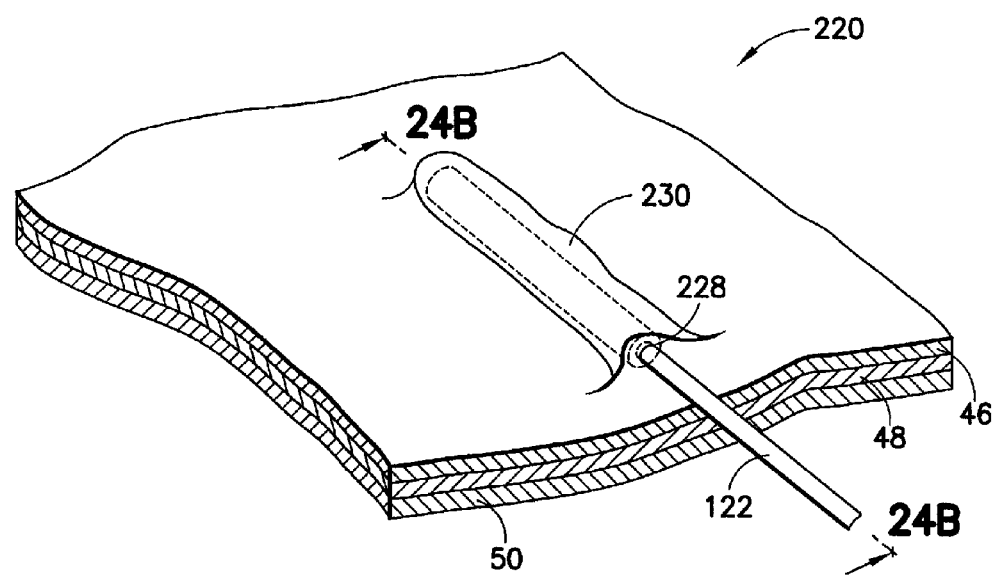
FIGS. 24A through 24D are perspective and cross sectional views showing a method of using a submucosal tunneling instrument according to an embodiment of a submucosal medical procedure system of the present invention.
Figure 24B:
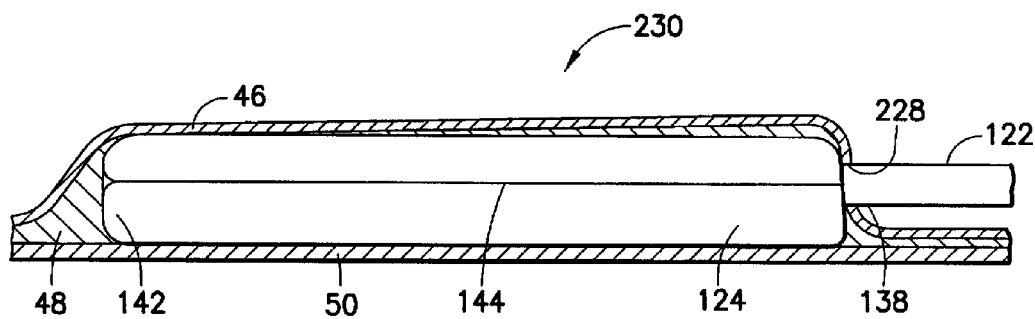
Figure 24C:
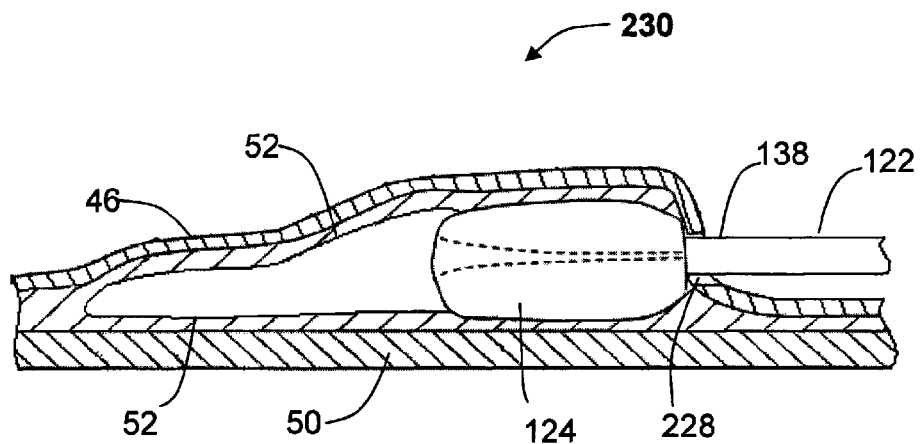
Figure 24D:
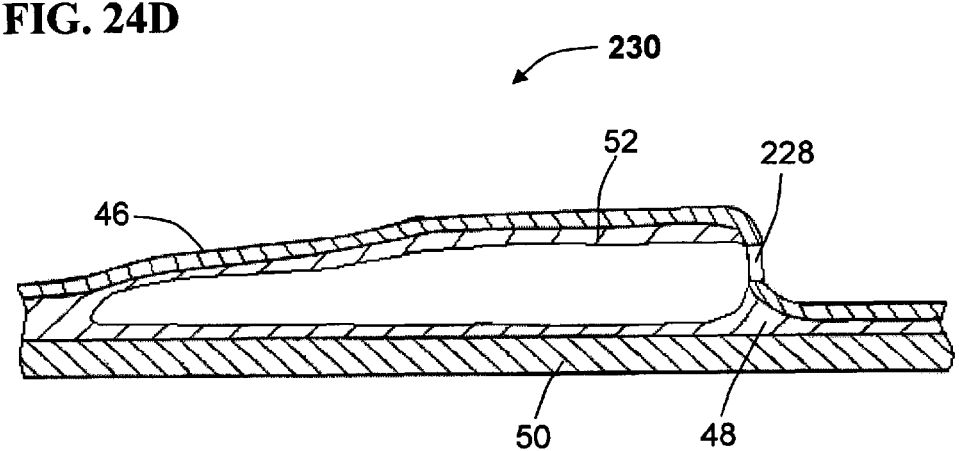

In order to perform a submucosal medical procedure, the target area in the digestive tract must be prepared to gain access to the submucosal space. FIGS. 21A and 21B illustrate a desired region 220 of the digestive tract of a mammal. A safe access needle injection instrument according to any of the embodiments previously described may be used to form a safety bleb 222 beneath the mucosal layer 46. The safety bleb contains the submucosal connective tissue 52 generally in a stretched condition attached to both the mucosal layer 46 and the muscular layer 50. As shown in FIGS. 22A and 22B, an endoscopic incision tool 224 is positioned adjacent to the safety bleb 222. An incision tool tip 226 of the endoscopic incision tool 224 is used to create a small mucosal opening 228 in the mucosal layer 46 of the safety bleb. The elevated mucosal layer 46 reduces the likelihood that the incision tool tip 226 will damage the underlying muscular layer 50. FIGS. 23A through 24D illustrate the introduction and operation of a submucosal tunneling instrument into submucosal layer 48. The distal end 138 of the submucosal tunneling instrument 120 is positioned through the mucosal opening 228. Once the proximal end 140 of balloon 124 is through the mucosal opening 228 the submucosal tunneling instrument 120 may be operated. By delivering pressurized fluid through the lumen of catheter 122, the proximal end 140 of balloon 124 inflates to its expanded diameter as depicted in FIG. 23C. Generally the expanded diameter of the proximal end 140 of balloon 124 is larger than the diameter of the mucosal opening 228. The larger diameter prevents balloon 124 from pushing the distal end 138 of catheter 122 backwards out of the submucosal layer 48 through mucosal opening 228. As shown in FIG. 23D, further inflation extends balloon 124 in a linear fashion within the submucosal layer 48 causing the submucosal connective tissue 52 to break in regions adjacent to the balloon. The balloon 124 can only expand by increasing the volume of the surrounding area between the mucosal layer 46 and the muscular layer 50. The application of force during expansion of balloon 124 is concentrated on the submucosal connective tissue 52, thereby causing the submucosal connective tissue 52 to break, whereas the force applied to the mucosal layer 46 or the muscular layer 50 by balloon 124 is diluted over a larger portion of balloon 124. The force required to break the submucosal connective tissue 52 as applied by balloon 124 is less than the force required to perforate the mucosal layer 46 or muscular layer 50 by balloon 124 thereby minimizing trauma to surrounding tissue. FIG. 24A illustrates a perspective view of region 220 in the digestive tract having a submucosal tunnel 230 formed by submucosal tunneling instrument 120. As shown in FIG. 24B, balloon 124 is fully expanded and generally occupies the majority of the space of submucosal tunnel 230. Balloon 124 is then deflated by applying a negative pressure to catheter 122 and retracting tether member 144. The distal end 138 of catheter 122 is then removed from mucosal opening 228, leaving submucosal tunnel 230 generally deflated. The submucosal connective tissue 52 within the tunnel is broken. For some submucosal medical procedures the submucosal tunnel 230 may provide suitable access to the muscular wall or the placement of an implant device. However to perform other submucosal medical procedures an area larger than the submucosal tunnel 230 may be desired.

Figure 25A:
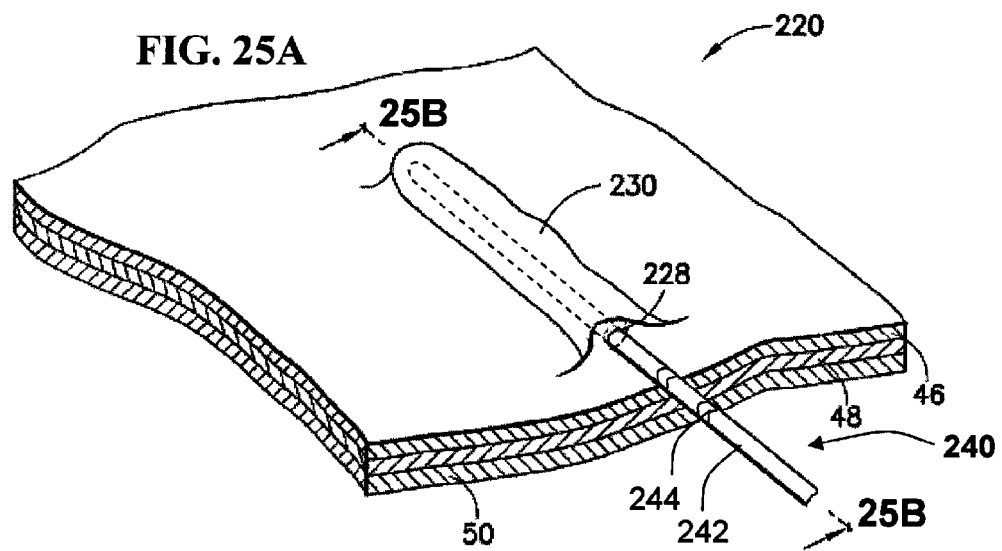
FIGS. 25A through 25D are perspective and cross sectional views showing a method of using a submucosal dissection instrument in a submucosal tunnel according to an embodiment of a submucosal medical procedure system of the present invention.
Figure 25B:
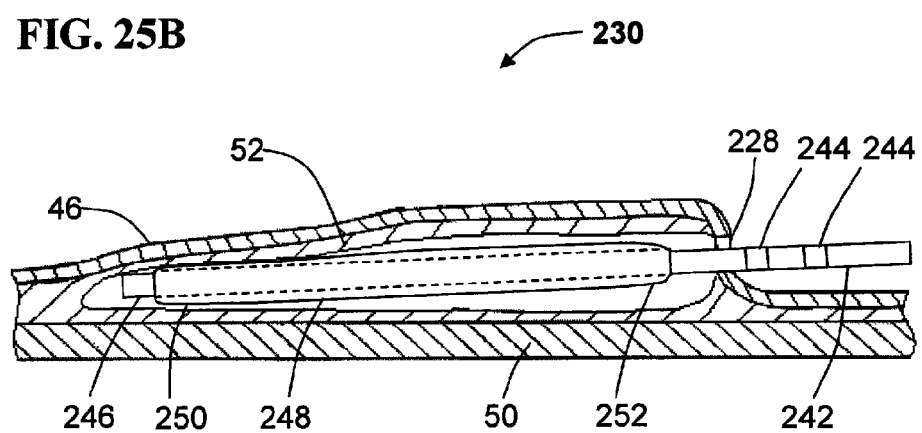
Figure 25C:
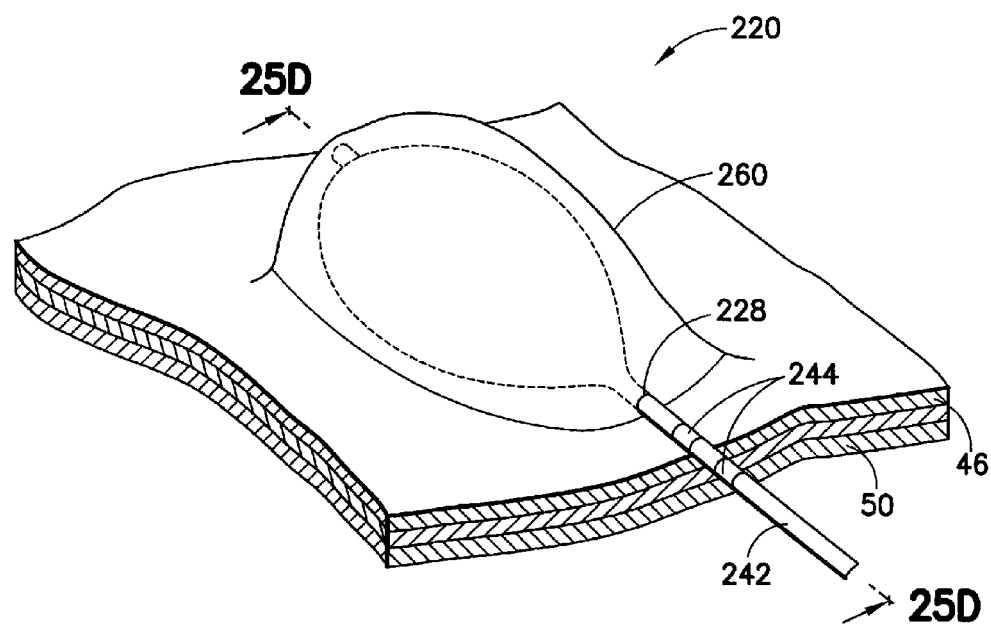
Figure 25D:
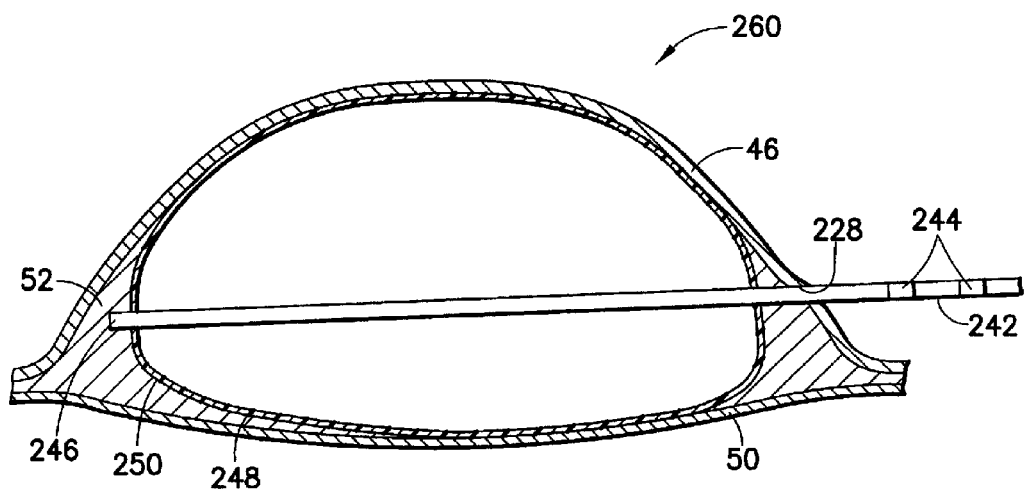

FIGS. 25A through 25D illustrate the formation of an area larger than a submucosal tunnel for performing a submucosal medical procedure according to an embodiment of the present invention. A region 220 in the digestive tract is prepared by forming a submucosal tunnel 230. A submucosal dissection instrument 240 having a catheter 242 is positioned through mucosal opening 228 into submucosal tunnel 230. Located on catheter 242 are markers 244 that indicate the insertion depth of catheter distal end 246 within submucosal tunnel 230. The submucosal dissection instrument 240 is in a proper position for operation when balloon member 248 including distal end 250 and proximal end 252 are sufficiently located within submucosal tunnel 230, as shown in FIG. 25B. As pressurized fluid is applied to a lumen in catheter 242 that is in fluid communication with balloon member 248, balloon member 248 inflates. During the expansion of balloon member 248, the submucosal connective tissue 52 is broken in the area of the expanded balloon member 248 and the mucosal layer 46 is elevated. The elevated mucosal layer 46 forms a large mucosal dissected area 260. After full expansion the balloon member 248 may be deflated and submucosal dissecting instrument 240 removed from the large mucosal dissected area 260. The dissected region beneath mucosal layer 46 has transformed in geometry from a high aspect ratio tunnel to a low aspect ratio chamber suitable for performing some submucosal medical procedures.

Figure 26:
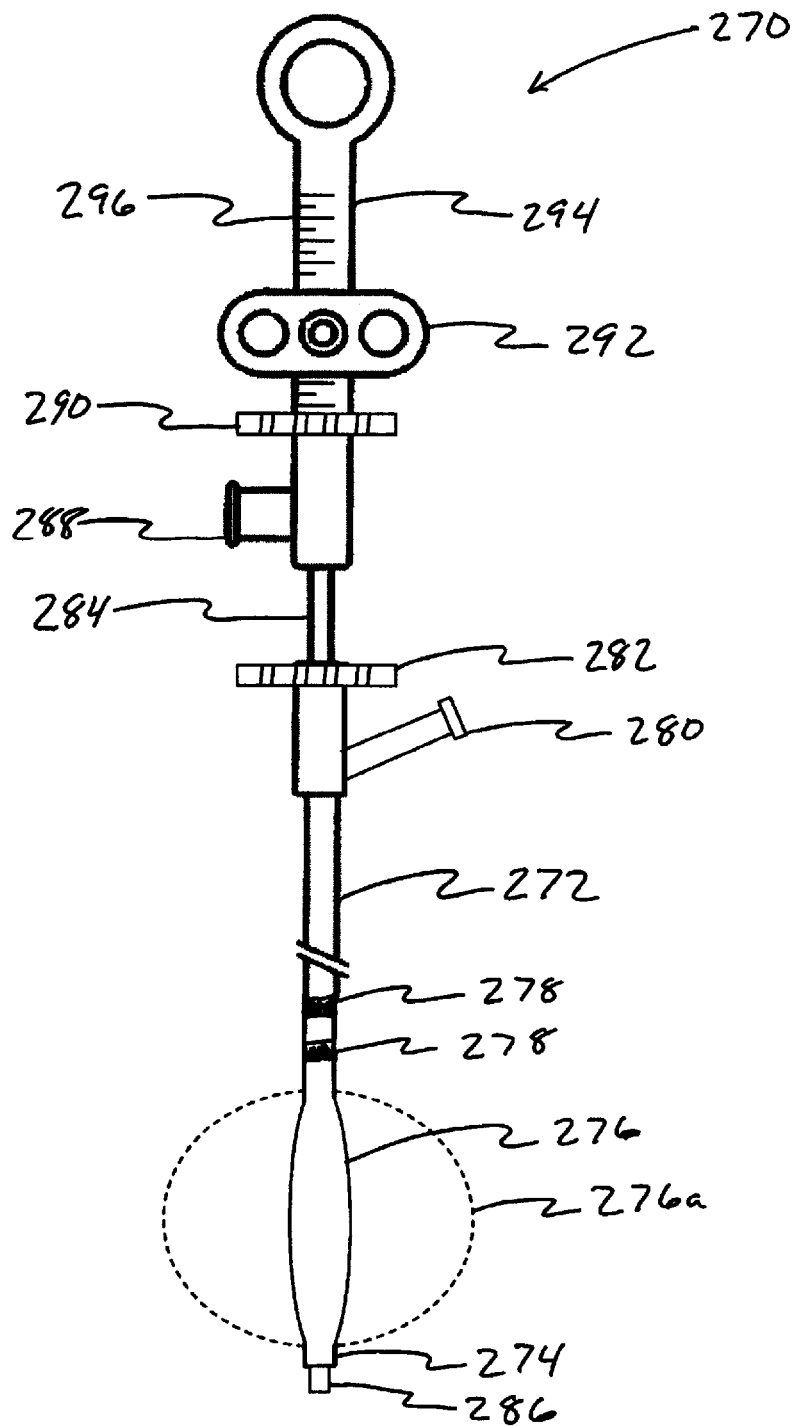
FIG. 26 is a side view showing a combined submucosal tunneling and dissection instrument according to an embodiment of a submucosal medical procedure system of the present invention.
Figure 27:
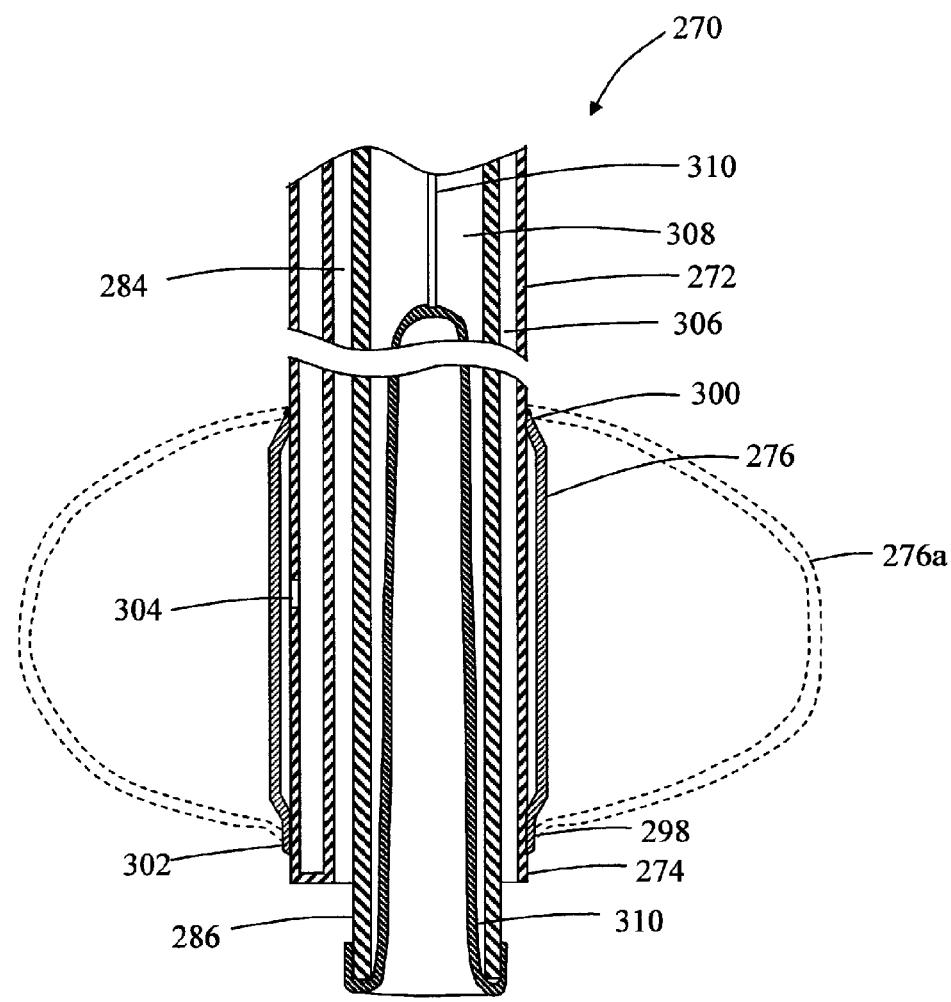
FIG. 27 is a broken cross-sectional view of a combined submucosal tunneling and dissection instrument according to an embodiment of a submucosal medical procedure system of the present invention.

Aforementioned descriptions of submucosal tunneling instruments and submucosal dissecting instruments have shown separate instruments to create a submucosal tunnel or large mucosal dissected area however the two types of instruments may be combined to form a submucosal tunneling dissecting instrument 270 as illustrated in FIG. 26. The submucosal tunneling dissecting instrument 270 includes a dissection catheter 272 having a distal end 274 and a dissection balloon 276 having an expanded dissection balloon 276a configuration. The dissection balloon 276 can be compliant of the type generally known in the art or dissection balloon 276 may be of the compliant or semi-compliant type. The dissection balloon 276 may be formed from biocompatible polymer types such as olefins, elastomers, thermoplastic elastomers, vinyls, polyamides, polyimides, polyesters, fluropolymers, copolymers and blends of any of the aforementioned. The dissection catheter 272 has insertion markers 278 positioned along its shaft. The proximal end of dissection catheter 272 includes both an inflation port 280 that is in fluid communication with dissection balloon 276, and a valve assembly 282. Tunneling catheter 284 is slidably disposed through valve assembly 282 extending within a lumen of dissection catheter 272. The tunneling catheter distal end 286 may extend beyond the dissection catheter distal end 274. Tunneling catheter 284 includes an inflation port 288 and valve assembly 290. A tether slide member 292 is slidably disposed on handle body 294 with distance markers 296. FIG. 27 illustrates a detailed cross section of the distal portion of the submucosal tunneling dissecting instrument 270. The distal end 298 and proximal end 300 of dissection balloon 276 are connected to the exterior of dissection catheter 272. Inflation lumen 302 connects inflation port 280 with the interior of dissection balloon 276 through inflation aperture 304. Tunneling catheter 284 is slidably disposed within the lumen 306 of dissection catheter 272. Positioned within the lumen 308 of tunneling catheter 284 there is an everted expandable tunneling balloon 310. The tunneling balloon 310 is preferably non-compliant of the type generally known in the art, however, tunneling balloon 310 may be of the compliant or semi-compliant type. The tunneling balloon 310 may be formed from biocompatible polymer types such as olefins, elastomers, thermoplastic elastomers, vinyls, polyamides, polyimides, polyesters, fluropolymers, copolymers and blends of any of the aforementioned. The distal end of tunneling balloon 310 is connected to a tether member 312 which has a proximal end that is connected to tether slide 292.

The operation of the submucosal tunneling dissecting instrument 270 to form a submucosal tunnel and large mucosal dissected area is similar to the operation of the separate instruments. In general, the distal end 286 of tunneling catheter 284 is positioned through a mucosal opening formed in a safety bleb. The tunneling catheter 284 is pressurized with fluid to linearly expand tunneling balloon 310. Once a submucosal tunnel has been formed tunneling balloon 310 may be deflated and dissection catheter 272 may be advanced through the mucosal opening into the submucosal tunnel. The markers 278 may be used to determine the depth in which the dissection catheter 272 has been advanced into the submucosal tunnel. Once the dissection catheter 272 has been properly positioned within the submucosal tunnel it may be operated. By applying pressurized fluid to inflation port 280, dissection balloon 276 is dilated to an expanded dissection balloon 276a configuration. During the expansion a large mucosal dissected area is created which is accessible for performing a subsequent submucosal medical procedure.

Another embodiment of the present invention includes a submucosal implant device for diagnosing and treating disorders of the body. The submucosal implant device may be a passive or active device. Active devices may include self contained electronics for controlling the device, as well as an internal power supply. Alternatively, the active devices may be controlled externally by telemetry. A passive submucosal implant device may take the form of a drug delivery depot in which a therapeutic agent within the depot elutes from the depot according to a predetermined elution profile. An active submucosal implant device may take the form of a drug delivery device that incorporates a self contained diagnostic system to determine the appropriate delivery time and dosage of a therapeutic agent to be administered. The passive or active submucosal implant device which takes the form of a drug delivery device may include a port positioned through the mucosal layer to allow endoscopic refilling of the drug delivery device with therapeutic agents. Submucosal implant devices that are drug delivery devices have the ability to deliver therapeutic agents directly to the portal circulation. Many different types of therapeutic agents may be delivered such as pharmaceuticals, hormones, growth factors and other biological compounds. Some typical therapeutic agents for use in a submucosal implant device of the present invention include dromostanolone, dromostanolone propionate, chlormadinone, chlormadinone acetate, dimethisterone, ethisterone, hydroxyprogesterone, norgestomet and other norsteroids such as norethindrone, norgesterone, northylodrel, norgestrel, noregestrienone, and norgestoniel; melengestrol acetate, estradiol, 17α-acetoxy-11β-methyl-19-norpregn-4-ene-3,20-dione, 3(3-oxo-11β,13β-dialkl-17β-hydroxygon-4-en-17α-yl)propionic acid-lactone, 3-(3-oxo-11βmethyl-17β-hydroxyestr-4-en-17α-yl)-propionic acid lactone, 11,13β-dialkyl-17 lower alkyl-17 lower alkyl-gon-4-en-3 one, 19-norpregn-4-ene-3,20-dione, oxytocin, vasopressin, adrenocorticotropic hormone, epidermal growth factor, prolactin, luliberin, luteinizing hormone releasing factor, growth hormone releasing factor, insulin, somatostatin, glucagon, interferon, gastrin, tetragastrin, pentagastrin, urogestrone, secretin, calcitonin, enkephalins, endorphins, angiotensins, renin, bradykinin, bacitracins, polymyxins, colistins, tyrocidin, gramicidines, synthetic analogues, modifications and pharmaceutically-active fragments of polypeptides, monoclonal antibodies, soluble vaccines, somatropin, somatotropin, cosyntropin, gonadotropins, chorionic gonadotropin, thyrotropin releasing hormone, thyroid stimulating hormone, pancreozymin and enkephalins.

By delivering therapeutics submucosally, some problems, such as digestion, which prevent the oral delivery of some therapeutic compounds, may be overcome. One such therapeutic compound that may be delivered through the submucosal implant device that cannot be administered orally is the hormone cholecytokinin (CCK). This hormone has been shown to be instrumental in triggering the brain to tell the body to stop eating by inducing satiety. As an appetite suppressant this compound may aid in the treatment of obesity.

An active submucosal implant device may take the form of a drug delivery device in which electrical signals are received from the contraction of the muscular wall of a mammal to deliver a specified amount of therapeutic agent. The submucosal implant may include an anchor member in which to secure the implant to the muscular wall beneath the mucosal layer. This anchor may be integrally formed with an electrode for receiving electrical signals from the wall. Multiple submucosal implant devices may be deposited at various locations along the stomach wall.

Figure 28:
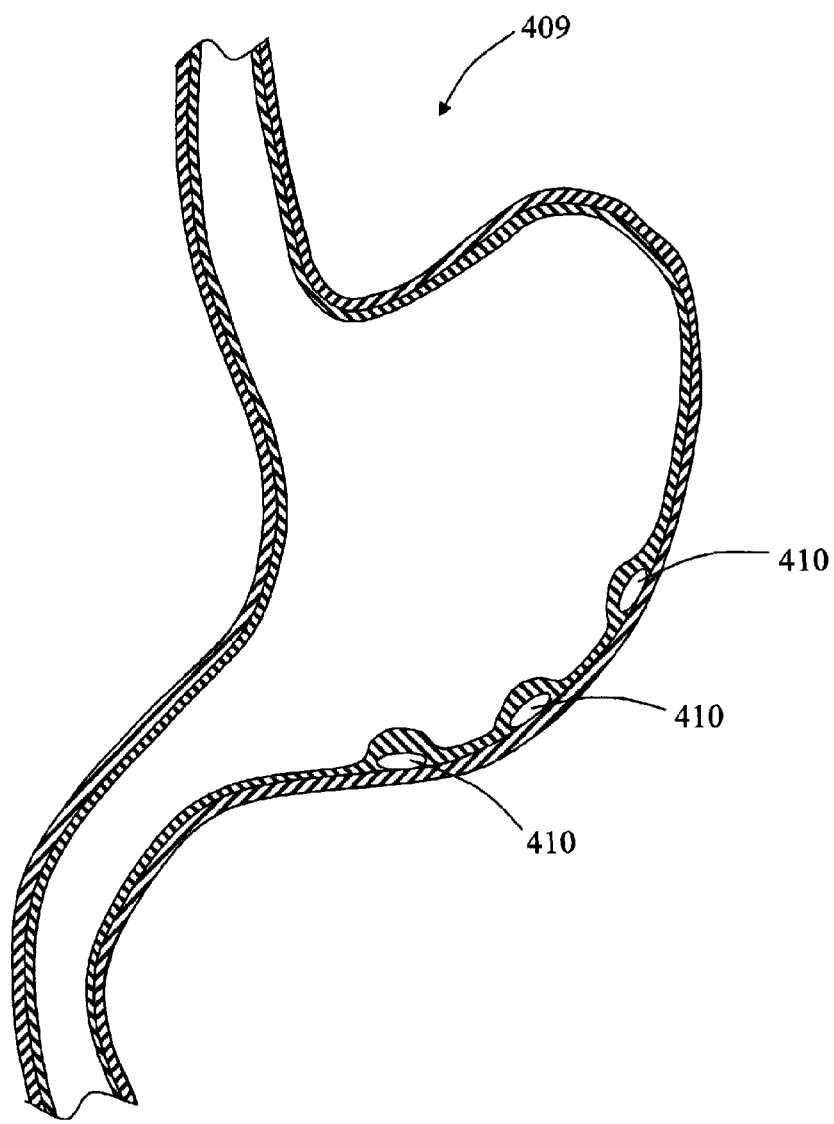
FIG. 28 is a cross-sectional view of the stomach showing a submucosal implant according to an embodiment of a submucosal medical procedure system of the present invention.
Figure 29A:
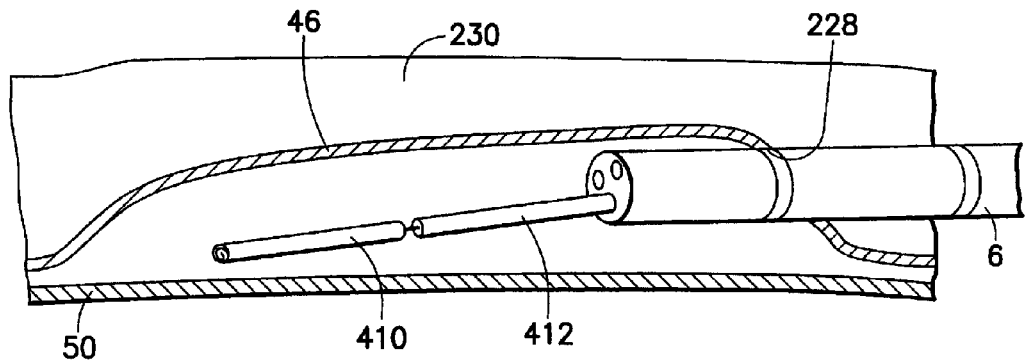
FIGS. 29A through 29C are partial cross-sectional perspective views showing a method of positioning a submucosal implant according to an embodiment of a submucosal medical procedure system of the present invention.
Figure 29B:
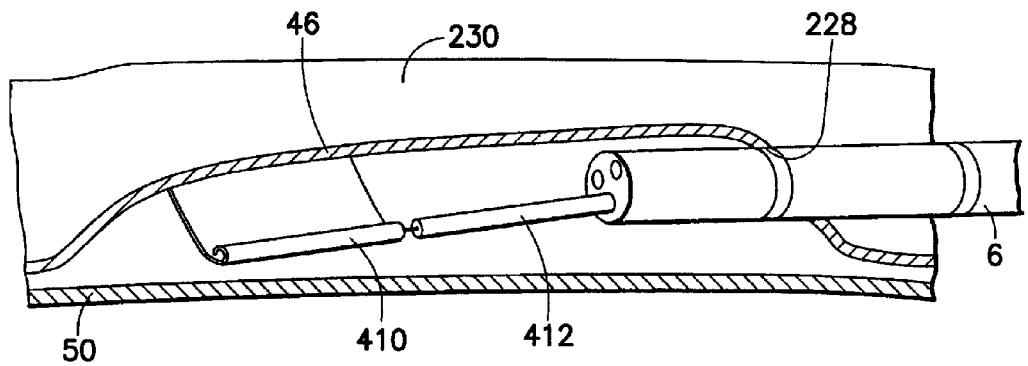
Figure 29C:
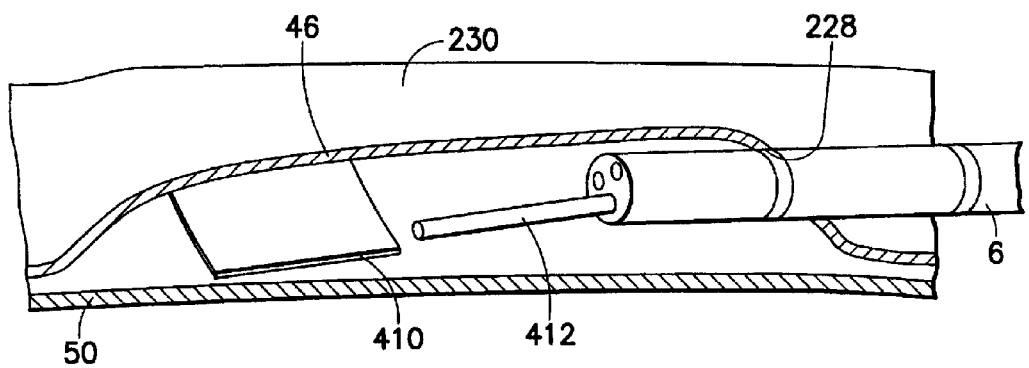

FIG. 28 shows a portion 409 of the digestive system in which a submucosal implant device 410 is placed within the wall of the stomach. FIGS. 29A through 29C illustrate a sequence for deploying a submucosal implant device according to an embodiment of the present invention. A submucosal tunnel 230 or a large mucosal dissected area is formed in a portion of the digestive tract. The insertion section 6 of an endoscope is positioned through an enlarged mucosal opening 228 into the submucosal space. The submucosal implant device 410 and an implant deployment device 412 are inserted through the mucosal opening 228 and preferably through a working channel of the endoscope into the submucosal space. Implant deployment device 412 is used to position submucosal implant device 410 within the submucosal space. Submucosal implant device 410 preferably takes the form of a drug delivery depot. The submucosal implant device may be in the form of a hydrogel, gel matrix, soluble wax or configurations commonly used in transdermal drug delivery devices. Submucosal implant device 410 is shown in a first configuration for delivery into the submucosal space and a second configuration for deployment adjacent muscular layer 50. Implant deployment device 412 is operated to move submucosal implant device 410 from its first configuration to the second configuration. Implant deployment device 412 then releases submucosal implant device 410 into the submucosal space. The implant deployment device 412 and endoscope insertion section 6 are then removed from the submucosal space and the mucosal opening 228 is then closed using clips, suture or other closure techniques.

Figure 30A:
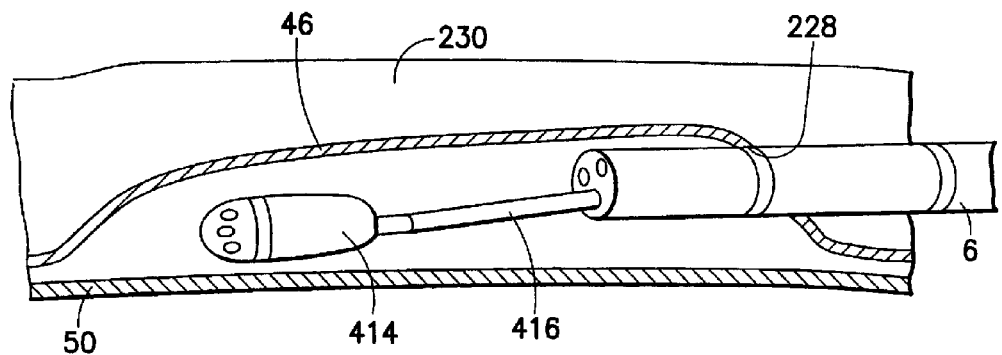
FIGS. 30A through 30C are partial cross-sectional perspective views showing a method of positioning a submucosal implant according to another embodiment of a submucosal medical procedure system of the present invention.
Figure 30B:
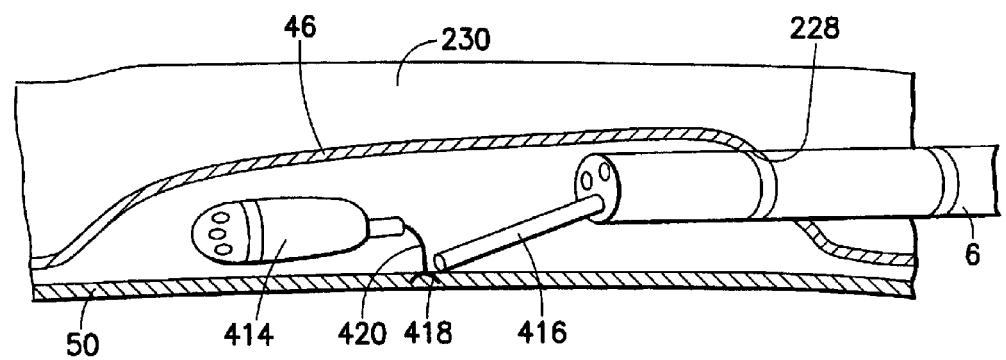
Figure 30C:
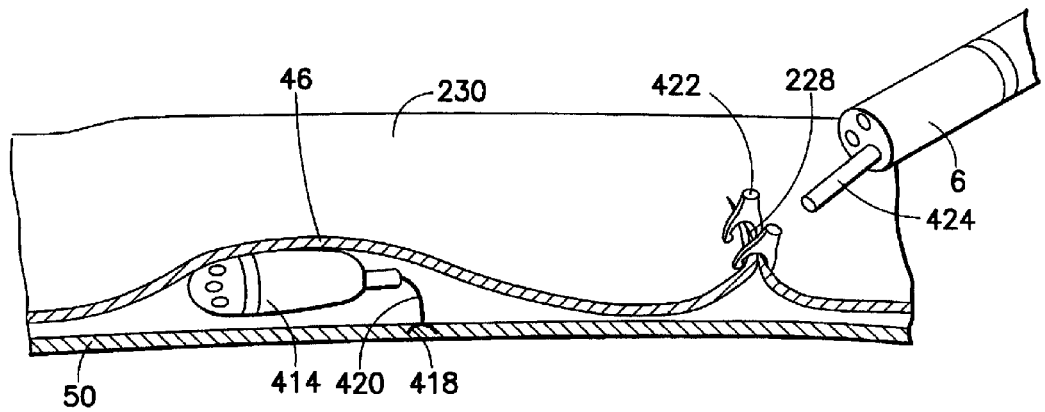
Figure 31A:
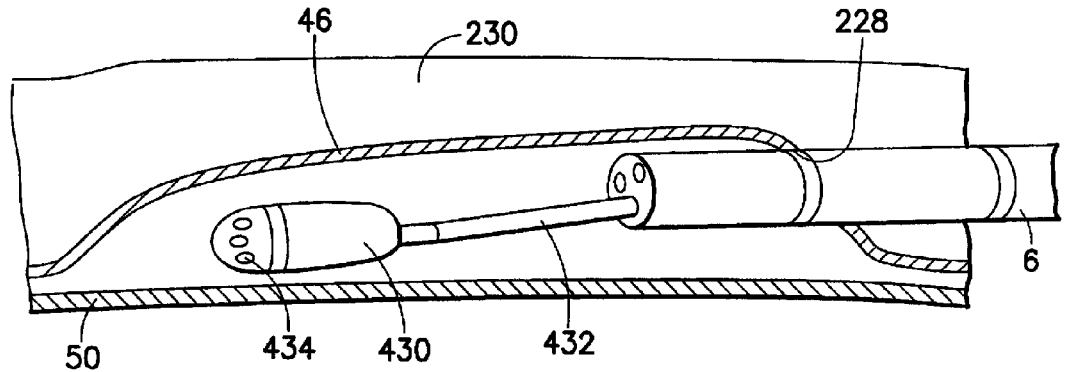
FIGS. 31A through 31F are partial cross-sectional perspective views showing a method of delivering a submucosal implant to a desired location within the digestive tract according to yet another embodiment of a submucosal medical procedure system of the present invention.
Figure 31B:
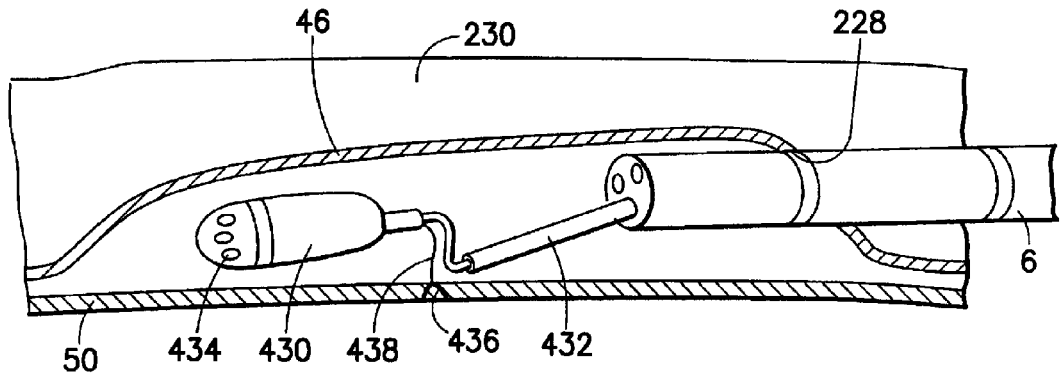
Figure 31C:
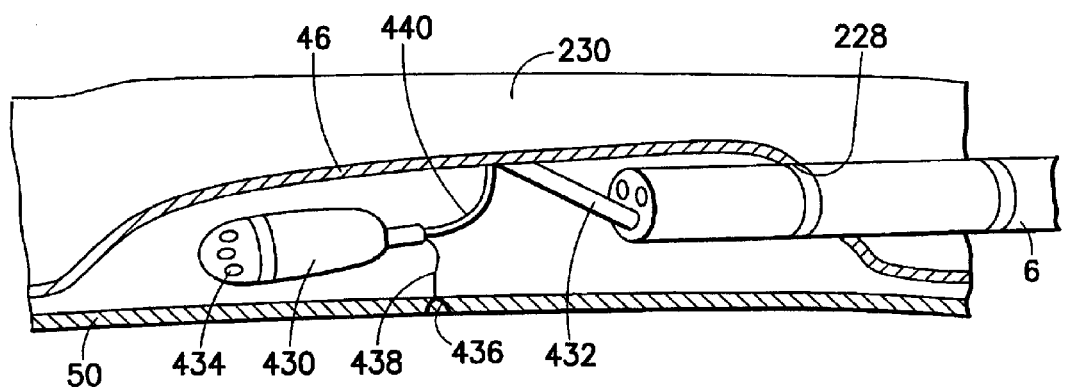
Figure 31D:
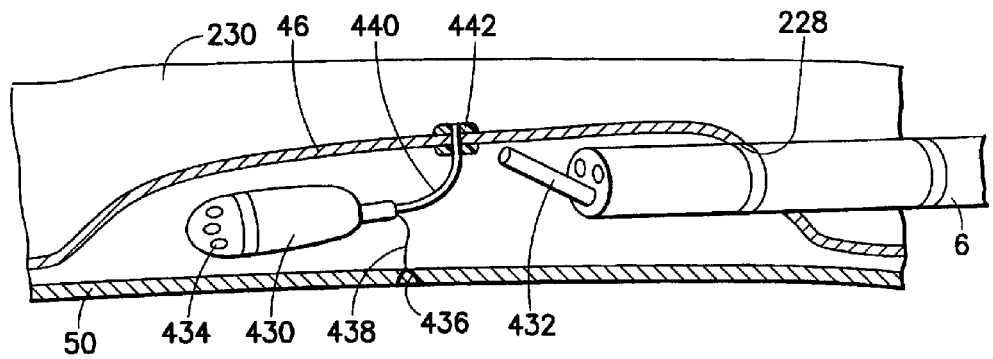
Figure 31E:
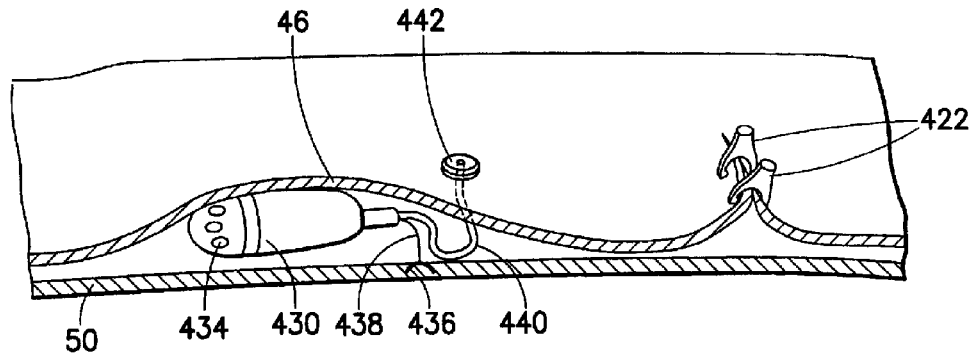
Figure 31F:
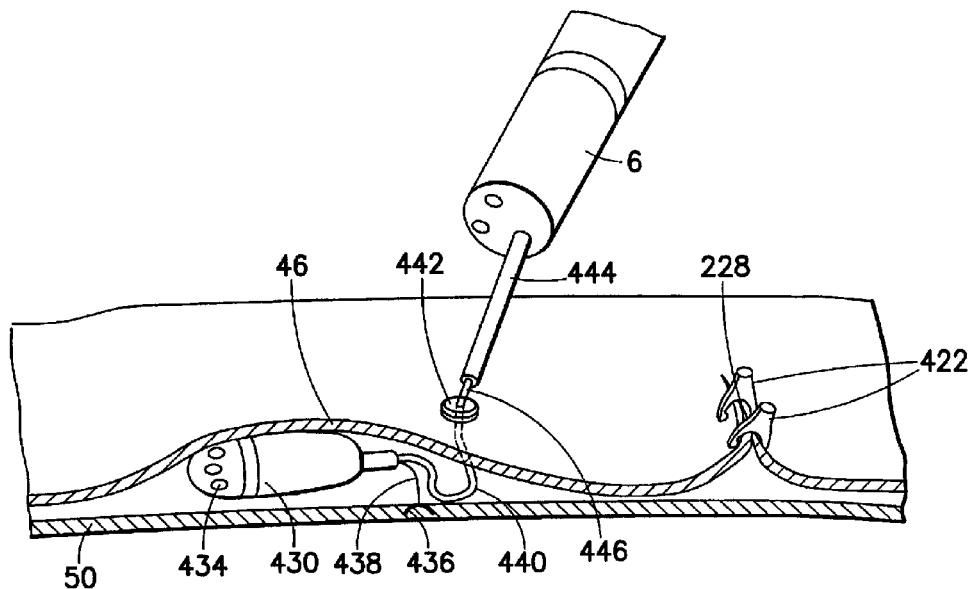

FIGS. 30A through 30C illustrate a submucosal implant device and sequence for deploying the device according to another embodiment of the present invention. A submucosal tunnel 230 or a large mucosal dissected area is formed in a portion of the digestive tract. The insertion section 6 of an endoscope is positioned through an enlarged mucosal opening 228 into the submucosal space. The submucosal implant device 414 and an implant deployment device 416 are inserted through the mucosal opening 228 and preferably through a working channel of the endoscope into the submucosal space. The relative sizes shown are for clarity; in practice, implant device be relatively smaller to permit passage through the working channel Implant deployment device 416 is used to position submucosal implant device 414 within the submucosal space. Submucosal implant device 414 also includes an anchor member 418 and a tether member 420. Anchor member 418 is adapted to be affixed to the muscular layer 50 and retain the submucosal implant device 414 in position by tether member 420. Submucosal implant device 414 preferably takes the form of a drug delivery device. In addition to performing anchoring and tethering functions, anchor member 418 and tether member 420 also function as an electrode and electrical conductor respectively. Electrical signals may be received by the submucosal implant device 414 from muscular layer 50 via anchor member 418 and tether member 420. Implant deployment device 416 then releases submucosal implant device 414 into the submucosal space. The implant deployment device 416 and endoscope insertion section 6 are then removed from the submucosal space and the mucosal opening 228 is then closed using closure clips 422 with a clip applier 424. Other closure techniques and devices such as sutures, staples and adhesives may also be suitable for closing mucosal opening 228.

FIGS. 31A through 31F illustrate another submucosal implant device and a sequence for deploying the device according to another embodiment of the present invention. A submucosal tunnel 230 or a large mucosal dissected area is formed in a portion of the digestive tract. The insertion section 6 of an endoscope is positioned through an enlarged mucosal opening 228 into the submucosal space. The submucosal implant device 430 and an implant deployment device 432 are inserted through the mucosal opening 228 and preferably through a working channel of the endoscope into the submucosal space. The relative sizes shown are for clarity; in practice, implant device be relatively smaller to permit passage through the working channel. Implant deployment device 432 is used to position submucosal implant device 430 within the submucosal space. Submucosal implant device 430 includes a therapeutic agent delivery port 434, an anchor member 436 and a tether member 438. Anchor member 436 is adapted to be affixed to the muscular layer 50 and retain the submucosal implant device 430 in position by tether member 438. Submucosal implant device 430 preferably takes the form of a therapeutic drug delivery device incorporating an internal drug reservoir. In addition to performing anchoring and tethering functions, anchor member 436 and tether member 438 also function as an electrode and electrical conductor respectively. Electrical signals may be sent and received by the submucosal implant device 430 to and from muscular layer 50 via anchor member 436 and tether member 438. The electrical signals may be used by the submucosal implant device 430 to initiate or terminate delivery of a therapeutic agent through delivery ports 434. Submucosal implant device 430 also includes a refill tube 440 connected to a mucosal port 442. Mucosal port 442 contains a valve assembly that can restrict fluid access to refill tube 440. Implant deployment device 432 positions the refill tube 440 within the submucosal space while the mucosal port 442 is positioned through mucosal layer 46. Implant deployment device 432 then releases submucosal implant device 430 into the submucosal space. The implant deployment device 432 and endoscope insertion section 6 are then removed from the submucosal space and the mucosal opening 228 is then closed using closure clips 422 with a clip applier 424. Other closure techniques and devices such as sutures, staples and adhesives may also be suitable for closing mucosal opening 228. The endoscope and related materials may then be removed from the patient. At a later time period, after the reservoir of submucosal implant device 430 has been depleted the physician may return endocopically to the site of the implant and use a refilling instrument 444 having a tip 446 that engages the mucosal port 442 to deliver more drugs to refill the reservoir.

Novel instruments, systems and methods have been disclosed to perform submucosal medical procedures in the digestive tract of a mammal. Although preferred embodiments of the invention have been described, it should be understood that various modifications including the substitution of elements or components which perform substantially the same function in the same way to achieve substantially the same result may be made by those skilled in the art without departing from the scope of the claims which follow.

What is claimed is:

1. A submucosal implant system comprising:
   a) a safe access needle injection means having a needle member adapted to pierce a mucosal tissue and deliver fluid to a submucosal layer;
   b) a submucosal tunneling means including an elongate tubular member having proximal and distal ends and a lumen extending therethrough and an expandable member having first and second ends wherein said first end of said expandable member is attached to said distal end of said tubular member and said second end of said expandable member is everted and positioned within said lumen of said tubular member,
   wherein said distal end of said elongate tubular member is adapted to enter an opening through the mucosal layer and into the submucosal layer of a mammal;
   c) a submucosal dissection means including an elongate tubular member having proximal and distal sections and an expandable member disposed at said distal section of said tubular member; and,
   d) an implantable therapeutic agent delivery device.

2. A submucosal implant system according to claim 1 wherein said safe access needle injection means comprises:
   an elongate tubular member having proximal and distal ends and a lumen extending therethrough;
   a tissue holding member positioned adjacent the distal end of said elongate tubular member and is adapted to engage a desired region of a mucosal layer; and,
   said needle member having a lumen wherein said needle member is slidably disposed within the lumen of said elongate tubular member and adapted to pierce a desired region of the mucosal layer engaged by said tissue holding member and enter the submucosal layer such that delivery of a fluid through the lumen of said needle member enters said submucosal layer to thereby elevate said desired region of the mucosal layer.

3. A submucosal implant system according to claim 1 wherein said submucosal dissecting means comprises an elongate tubular member having proximal and distal sections and an expandable member disposed at the distal section of said tubular member.

4. A submucosal implant system according to claim 1 wherein said submucosal tunneling means and said submucosal dissecting means are integrally formed.

5. A submucosal implant system according to claim 1 wherein said implantable therapeutic agent delivery device includes an anchor.

6. A submucosal implant system, comprising:
   a) a safe access needle injection means having a needle member adapted to pierce mucosal tissue and deliver fluid to the submucosal layer;
   b) a submucosal tunneling means including an elongate tubular member having proximal and distal ends and a lumen extending therethrough, and an expandable member having first and second ends wherein said first end of said expandable member is attached to said distal end of said tubular member and said second end of said expandable member is everted and positioned within said lumen of the tubular member,
   wherein the distal end of said elongate tubular member is adapted to enter an opening through the mucosal layer and into the submucosal layer of a mammal;
   c) a submucosal dissection means including an elongate tubular member having proximal and distal sections and an expandable member disposed at the distal section of said tubular member; and,
   d) an implantable drug delivery device.

7. A submucosal implant system according to claim 6 wherein said safe access needle injection means comprises:
   an elongate tubular member having proximal and distal ends and a lumen extending therethrough;

a tissue holding member positioned adjacent the distal end of said elongate tubular member and is adapted to engage a desired region of a mucosal layer; and, said needle member having a lumen wherein said needle member is slidably disposed within the lumen of said elongate tubular member and adapted to pierce a desired region of the mucosal layer engaged by said tissue holding member and enter the submucosal layer such that delivery of a fluid through the lumen of said needle member enters said submucosal layer to thereby elevate said desired region of the mucosal layer.

8. A submucosal implant system according to claim 6 wherein said implantable drug delivery device includes an anchor.

9. A submucosal implant system, comprising:
a) a safe access needle injection instrument having a needle member adapted to pierce mucosal tissue and deliver fluid to the submucosal layer;
b) a submucosal tunneling device having an expandable, evertable distal end;
c) a submucosal dissection device having an expandable distal end,
   wherein each of said tunneling device and said dissection device has a closed distal end; and
d) an implantable drug delivery device.

10. A submucosal implant system according to claim 9 wherein said distal end of said tunneling device is longitudinally expanding, and said distal end of said dissection device is laterally expandable.

11. A submucosal implant system according to claim 9 wherein said implantable drug delivery device includes an anchor.

12. A submucosal implant system according to claim 11 wherein said implantable drug delivery device includes an anchor.

13. A submucosal implant system, comprising:
a) a safe access needle injection means having a needle member adapted to pierce mucosal tissue and deliver fluid to the submucosal layer;
b) a submucosal tunneling means having a distal end with a longitudinally expandable, evertable tip;
c) a submucosal dissection means including an elongate tubular member having proximal and distal sections, an expandable member disposed at said distal section of said tubular member, and an open distal end,
   wherein said expandable tip of said tunneling means is longitudinally displaceable through said open distal end and relative to said expandable member of said dissection means; and
d) an implantable drug delivery device.

14. A submucosal implant system according to claim 13, wherein said submucosal tunneling means and said submucosal dissecting means are integrally formed.

* * * * *